United States Patent [19]

Enomoto et al.

[11] Patent Number: 4,711,898

[45] Date of Patent: Dec. 8, 1987

[54] 4-QUINOLONE DERIVATIVES HAVING ANTI-INFLAMMATORY, ANTI-ALLERGIC, ANTITUSSIVE, EXPECTORANT AND ANTITHROMBOTIC ACTIVITY

[75] Inventors: Hiroshi Enomoto, Nagoakakyo; Tadatoshi Nomura, Uji; Yoshiaki Aoyagi, Otsu; Shoichi Chokai, Kameoka; Yukio Fujita, Takatsuki; Tatsuhiko Kono, Suita; Masao Murase, Kusatsu; Kichiro Inoue, Kyoto; Masahiro Adachi, Hirakata, all of Japan

[73] Assignee: Nippon Shinyaku Co., Ltd., Japan

[21] Appl. No.: 781,142

[22] Filed: Sep. 27, 1985

Related U.S. Application Data

[63] Continuation of Ser. No. 504,246, Jun. 14, 1983, abandoned.

[30] Foreign Application Priority Data

Jun. 14, 1982 [JP] Japan ................................ 57-102592

[51] Int. Cl.$^4$ ..................... A61K 31/47; C07D 215/48
[52] U.S. Cl. .................................. 514/312; 546/153; 560/43; 560/51
[58] Field of Search ........................ 546/153; 514/312

[56] References Cited

U.S. PATENT DOCUMENTS

| | | | |
|---|---|---|---|
| 2,785,165 | 3/1957 | Schock | 546/153 X |
| 4,049,715 | 9/1977 | Bell | 514/312 X |
| 4,476,132 | 10/1984 | Göschke et al. | 514/312 |

FOREIGN PATENT DOCUMENTS 1202105  1/1960  France ................................ 546/153

OTHER PUBLICATIONS

Schock, J. Am. Chem. Soc., vol. 79, pp. 1672–1675 (1957).
Andersag, et al., Chemical Abstracts, vol. 48, 12183h (1954).
Joh, et al., Chemical Abstracts, vol. 73, 45294x, 45295y (1970).
DE No. 2,806,879 (cf. Chem. Abstr. 91, 211281j).
EP No. 62,001 (cf. Chem. Abstr. 98, 160599d).

*Primary Examiner*—Donald G. Daus
*Assistant Examiner*—Diana G. Rivers
*Attorney, Agent, or Firm*—Jacobs & Jacobs

[57] ABSTRACT

4-Quinolone derivatives of the present invention are useful for their anti-inflammatory, anti-allergenic, antitussive, expectorant and antithrombotic activity. Pharmaceutical compositions containing said compounds and pharmaceutically acceptable salts thereof and methods of treating humans and animals are described herein.

17 Claims, No Drawings

4-QUINOLONE DERIVATIVES HAVING ANTI-INFLAMMATORY, ANTI-ALLERGIC, ANTITUSSIVE, EXPECTORANT AND ANTITHROMBOTIC ACTIVITY

CROSS-REFERENCE

This is a continuation of Ser. No. 504,256 filed June 14, 1983, now abandoned.

The present invention is concerned with 4-Quinolone derivatives, processes for their production, pharmaceutical compositions wherein said compounds or pharmaceutically acceptable salts thereof are the active agent and to methods of effecting anti-inflammatory, anti-allergenic, anti-tussive, expectorant and anti-thrombotic action in humans and animals.

Sodium chromoglicate reported by Cox et al in *Advances in Drug Research*, vol. 5, p.115 (1970) is known to be effective for allergic asthma. However, that compound is believed to inhibit emission of chemical mediators from most cells but has the disadvantage that it does not show any effect on oral administration and the duration of its action is rather short.

*Drugs of Today*, vol. 14, no. 7, p.312 (1978) and *Annual Report in Medicinal Chemistry*, vol. 12, pp 76-77 (1977) also refer generally to substances having useful pharmaceutical properties.

It has been recently discovered that SRS-A (slow reacting substance of anaphylasix) which is one of the chemical mediators which plays a main role at the onset of asthma offers an area which, if one could develop new and specific pharmaceutical antagonizing agents against the action of SRS-A, a significant advance in the art would result.

More specifically, the present invention is concerned with compounds of the formula (I):

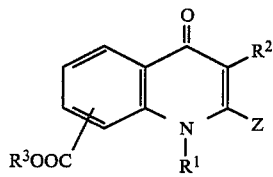

(I)

or a pharmaceutically acceptable salt thereof, wherein $R^1$ and $R^2$ are each hydrogen, alkyl of 1 to 8 carbon atoms or alkenyl of 2 to 4 carbon atoms; $R^3$ is hydrogen, alkyl of 1 to 8 carbon atoms unsubstituted or substituted by one or two hydroxyl moieties, alkyl of 3 to 10 carbon atoms with one or two ether bonds unsubstituted or substituted by 1 or 2 hydroxyl groups or —$(CH_2)_nA$ wherein n is an integer of 1 to 3 and A is acetyl, acetoxy ethoxycarbonyl, ethoxycarbonylacetyl, cyano or phenoxy phenethyl or allyl of 2 to 4 carbon atoms; and Z is phenyl unsubstituted or substituted by one or two halo atoms, one or two alkyl moieties of 1 to 8 carbon atoms, haloalkyl of 1 to 3 carbon atoms, one or two alkoxy moieties of 1 to 4 carbon atoms or $COOR^4$ wherein $R^4$ is hydrogen or alkyl of 1 to 4 carbon atoms; or Z is a 5- or 6-membered unsaturated heterocycle wherein said heteroatoms are selected from the group consisting of nitrogen, oxygen and sulphur. These compounds are useful for their anti-inflammatory activity, anti-allergic action, as antitussives, expectorants and as antithrombotic agents.

These compounds and their pharmaceutically acceptable salts are particularly useful because of their ability to provide the above therapeutic properties on oral administration, while conventional known agents are not effective on oral administration. In addition, the therapeutic action is is of a longer duration than compounds presently known in the art.

Examples of alkyl groups which are useful according to the present invention are methyl, ethyl, propyl, isopropyl, butyl, pentyl, hexyl, heptyl, octyl and the like. Examples of alkoxy groups useful according to the present invention are methoxy, ethoxy, propoxy, isopropoxy, butoxy, tert butoxy and the like. Examples of suitable alkenyl groups according to the present invention include vinyl and allyl. Suitable halo atoms include fluoro, chloro, bromo and iodo.

Suitable substituents for Z include phenyl, 2-fluorophenyl, 2-chlorophenyl, 3-chlorophenyl, 4-chlorophenyl, 2-bromophenyl, 2-iodophenyl, 2,4-dichlorophenyl, 3,4-dichlorophenyl, 2,5-dichlorophenyl, o-tolyl, p-tolyl, 2-ethylphenyl, 4-isopropylphenyl, 4-pentylphenyl, 2,4-dimethylphenyl, 3-trifluoromethylphenyl, 2-methoxyphenyl, 4-methoxyphenyl, 2-ethoxyphenyl, 2-isopropoxyphenyl, 2,4-dimethoxyphenyl, 3,4-dimethoxyphenyl, 4-carboxyphenyl, 4-methoxycarbonylphenyl, pyrrolyl, pyrrolinyl, pyridyl, furyl and thienyl.

A compound of the formula (I) may also exist in tautomeric form:

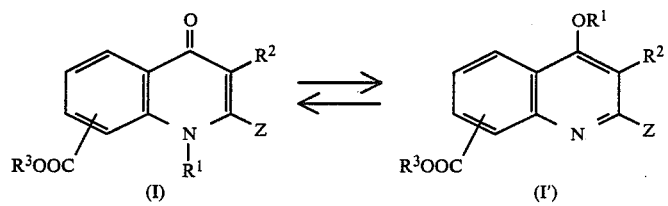

The compounds of the present invention and tautomers thereof may be prepared by a variety of methods. According to one process, compounds of the formula (II):

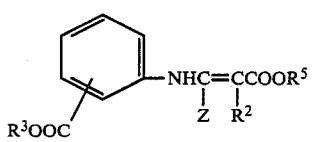

(II)

wherein $R^2$, $R^3$ and Z are as above defined; and $R^5$ is lower alkyl, are subjected to ring closure. Suitable, the reaction is conducted at an elevated temperature and the reactions are dissolved in a suitable solvent such as dichlorobenzene, tetraline, diphenyl ether, diethylene glycol dimethyl ether or the like for a period of from about 30 minutes to 10 hours.

In compounds of the formula (I) wherein R¹ is an alkyl or alkenyl group as above defined, such can be prepared by reacting a 4-quinolone derivative obtained by the above method with an alkyl halide having the corresponding number of carbon atoms in the alkyl moiety, a dialkyl sulfate having the corresponding number of carbon atoms in the alkyl moieties, or with an alkenyl halide having the corresponding number of carbon atoms in the alkenyl portion, in the presence of a suitable base or acid-removing agent. Suitable alkyl halides include methyl iodide, ethyl iodide, methyl bromide, ethyl bromide, propyl bromide, butyl bromide and the like. Suitable dialkyl sulfates include dimethyl sulfate, diethyl sulfate and the like. Examples of alkenyl halides include vinyl bromide, allyl bromide and the like. Examples of suitable bases or acid-removing agents include sodium carbonate, potassium carbonate, sodium bicarbonate, potassium bicarbonate, sodium hydroxide, potassium hydroxide, sodium alkoxides and sodium hydride.

The reaction is suitably carried out by heating the reactants in a suitable solvent, for example tetrahydrofuran, dioxane, toluene, xylene, dimethyl formamide, or dimethyl sulfoxide, at a temperature of from about 50° C. to about 120° C. for a period of from thirty minutes to ten hours.

Compounds of the formula (I) are also produced by subjecting a compound of the formula:

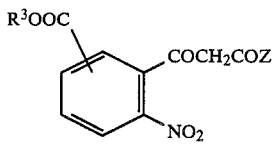

wherein $R^3$ is hydrogen, alkyl of 1 to 8 carbon atoms unsubstituted or substituted by one or two hydroxyl moieties, alkyl of 3 to 10 carbon atoms with one or two ether bonds or —$(CH_2)_nA$ wherein n is an integer of 1 to 3 and A is acetyl, acetoxy, cyano or phenoxy; and Z is phenyl unsubstituted or substituted by one or two halo atoms, one or two alkyl moieties of 1 to 8 carbon atoms, haloalkyl of 1 to 3 carbon atoms, one or two alkoxy moieties of 1 to 4 carbon atoms or COOR⁴ wherein R⁴ is hydrogen or alkyl of 1 to 4 carbon atoms, or Z is a 5- or 6-membered unsaturated heterocycle wherein said heteroatoms are selected from the group consisting of nitrogen, oxygen and sulphur, to a reduction action followed by ring closure.

Alternatively, compounds of the formula (I) may also be produced by subjecting a compound of the formula:

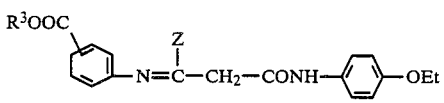

or a tautomer thereof wherein $R^3$ is hydrogen, alkyl of 1 to 8 carbon atoms unsubstituted or substituted by one or two hydroxyl moieties, alkyl of 3 to 10 carbon atoms with one or two ether bonds or —$(CH_2)_nA$ wherein n is an integer of 1 to 3 and A is acetyl, acetoxy, cyano or phenoxy; and Z is phenyl unsubstituted or substituted by one or two halo atoms, one or two alkyl moieties of 1 to 8 carbon atoms, haloalkyl of 1 to 3 carbon atoms, one or two alkoxy moieties of 1 to 4 carbon atoms or COOR⁴ wherein R⁴ is hydrogen or alkyl of 1 to 4 carbon atoms, or Z is a 5- or 6-membered unsaturated heterocycle wherein said heteroatoms are selected from the group consisting of nitrogen, oxygen and sulphur, to a ring closure reaction.

As a further alternative, compounds of the formula (I) are also produced by reacting a compound of the formula:

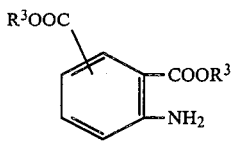

wherein $R^3$ is hydrogen, alkyl of 1 to 8 carbon atoms unsubstituted or substituted by one or two hydroxyl moieties, alkyl of 3 to 10 carbon atoms with one or two ether bonds or —$(CH_2)_nA$ wherein n is an integer of 1 to 3 and A is acetyl, acetoxy, cyano or phenoxy, with a compound of the formula:

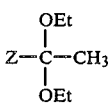

wherein Z is phenyl unsubstituted or substituted by one or two halo atoms, one or two alkyl moieties of 1 to 8 carbon atoms, haloalkyl of 1 to 3 carbon atoms, one or two alkoxy moieties of 1 to 4 carbon atoms or COOR⁴ wherein R⁴ is hydrogen or alkyl of 1 to 4 carbon atoms, or Z is a 5- or 6-membered unsaturated heterocycle wherein said heteroatoms are selected from the group consisting of nitrogen, oxygen and sulphur.

As a further alternative, compounds of the formula (I) are also purduced by reacting a compound of the formula:

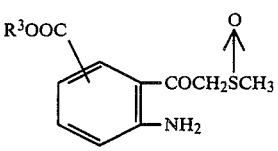

wherein $R^3$ is hydrogen, alkyl of 1 to 8 carbon atoms unsubstituted or substituted by one or two hydroxyl moieties, alkyl of 3 to 10 carbon atoms with one or two ether bonds or —$(CH_2)_nA$ wherein n is an integer of 1 to 3 and A is acetyl, acetoxy, cyano or phenoxy, with a compound of the formula ZCHO wherein Z is phenyl unsubstituted or substituted by one or two halo atoms, one or two alkyl moieties of 1 to 8 carbon atoms, haloalkyl of 1 to 3 carbon atoms, one or two alkoxy moieties of 1 to 4 carbon atoms or COOR⁴ wherein R⁴ is hydrogen or alkyl of 1 to 4 carbon atoms, or Z is a 5- or 6-membered unsaturated heterocycle wherein said heteroatoms are selected from the group consisting of nitrogen, oxygen and sulphur.

Compounds of the formula (II) may be obtained by condensation of a compound of the formula (III):

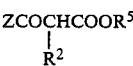 (III)

wherein $R^2$, $R^5$ and Z are as above defined with an aminobenzoate of the formula (IV):

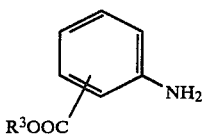 (IV)

wherein $R^3$ is as above defined. The raction is suitably conducted by heating the reactants in a suitable solvent such as benzene, toluene or chloroform in the presence of catalytic amounts of an acid such as p-toluenesulfonic acid, benzenesulfonic acid, sulfuric acid or hydrochloric acid for a period of from one day to three days, followed by dehydration using a Dienstag apparatus or by heating to reflux for one to three days in ethanol in the presence of activated anhydrous calcium sulfate.

Compounds of the formula (III) in which $R^2$ is alkyl or alkenyl as above defined can be prepared by the reaction of a compound of the formula (V):

$ZCOCH_2COOR^5$ (V)

wherein $R^5$ and Z are as above defined with an alkyl halide or alkenyl halide as above referred to in the presence of a suitable base. The reaction is carried out by stirrling the reactants in a suitable solvent such as, for example, benzene, toluene, tetrahydrofuran, methanol, ethanol, dimethyl formamide or acetonitrile at a temperature of from about $-5°$ C. to about $80°$ C. for a period of from about 30 minutes to about 5 hours. Suitable bases include sodium hydride and sodium alkoxide. Suitable alkyl halides include methyl iodide, ethyl iodide, methyl bromide, ethyl bromide, propyl bromide and butyl bromide. Suitable alkenyl halides include vinyl bromide and allyl bromide. The benzoyl acetate derivatives of the formula (V) used as starting materials in the above reaction include both known compounds and novel compounds.

Compounds of the formula (V) may be prepared as follows: Acetyl compounds of the formula (VI):

$ZCOCH_3$ (VI)

wherein Z is as above defined are reacted with a dialkylcarbonate such as dimethyl carbonate or diethyl carbonate in a suitable solvent such as ether or tetrahydrofuran in the presence of a suitable base such as sodium hydride or sodium amide. Alternatively, the acetate may be reacted with n-butyl lithium in the presence of cyclohexyl isopropylamine followed by a reaction with an acid chloride of the formula (VII):

ZCOCl (VII)

wherein Z is as above defined in a suitable solvent such as ether or tetrahydrofuran.

Examples of other synthetic routes include the following. Acetoacetate is reacted with an acid chloride of the formula (VII) in the presence of a base in a suitable solvent such as water or tetrahydrofuran and then deacetylated with ammonium chloride. Alternatively, acetoacetate in the form of an alkali metal salt is reacted with benzoate followed by deacetylation.

The compounds of the present invention when prepared by the above methods may be easily isolated and readily purified by conventional procedures such as recrystallization and chromatography.

Pharmaceutically acceptable salts of the compounds of the formula (I) may be prepared in a conventional manner. For example, compounds of the formula (I) wherein $R^3$ is hydrogen may be reacted with a suitable base such as sodium hydroxide, potassium hydroxide, potassium aluminum hydroxide, calcium hydroxide, sodium carbonate, potassium carbonate, sodium bicarbonate, potassium bicarbonate and other inorganic basic compounds as well as organic basic compounds such as morpholine, piperazine, thiomorpholine, triethylamine and the like to produce pharmaceutically acceptable salts. Suitable salts also include salts with mineral acids or organic acids. A typical example of a salt is ethyl 2-(2-chlorophenyl)-4-hydroxyquinoline-8-carboxylate hydrochloride.

The following example represents a synthetic route for producing compounds of the formula (I):

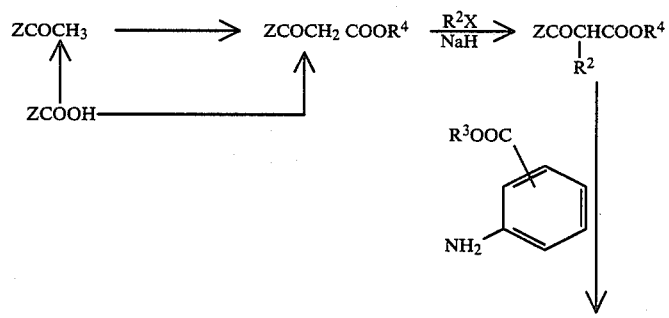

-continued
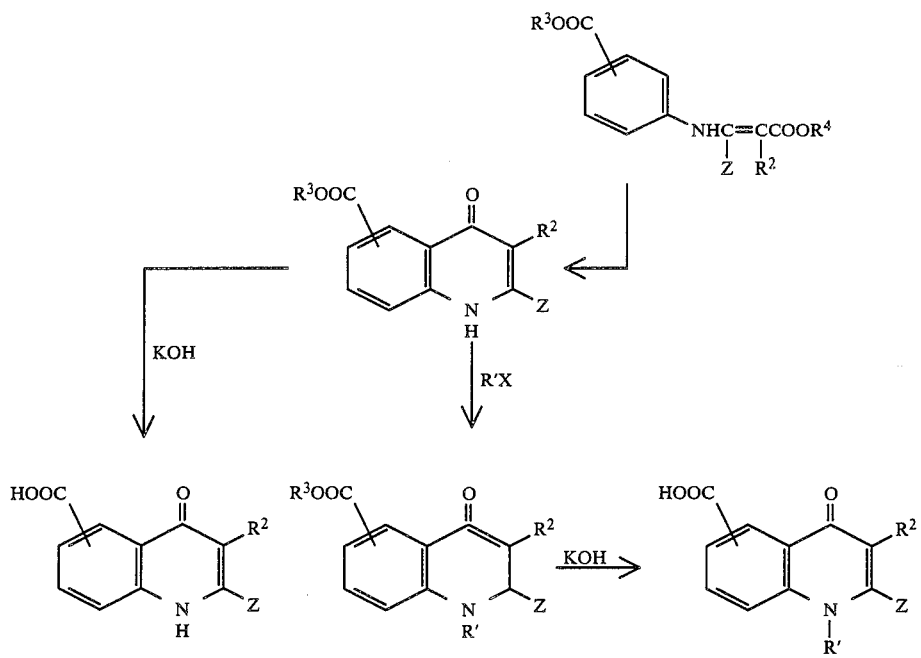
Alternatively, compounds of the formula (I) may also be prepared by the following route:
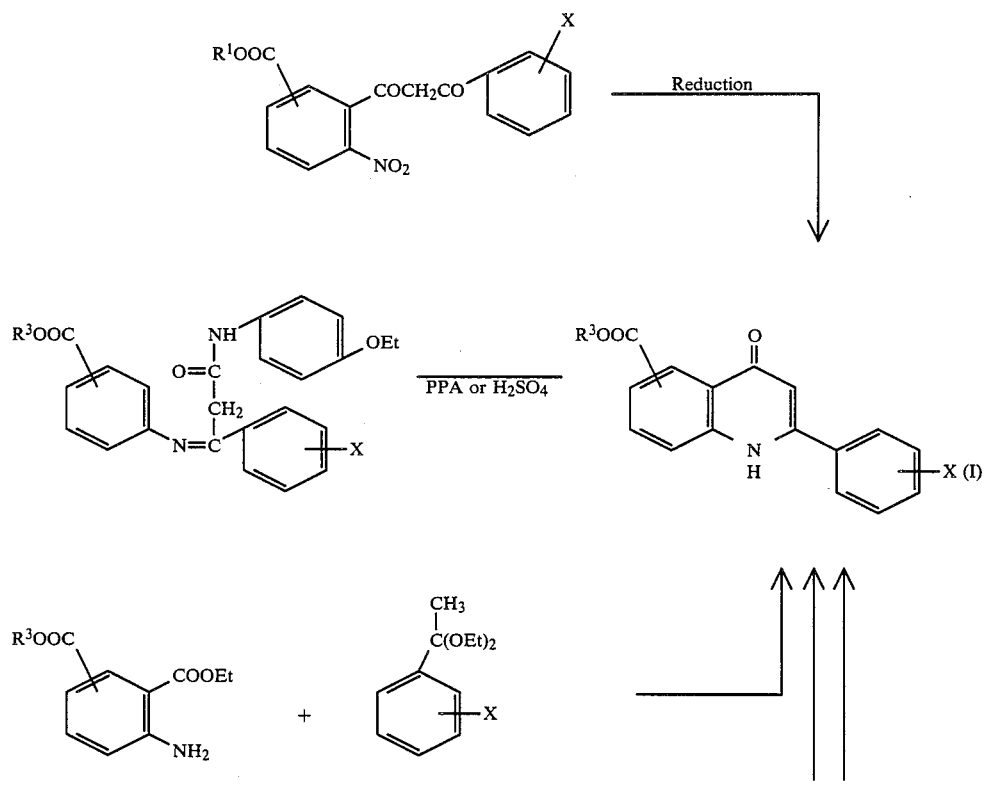

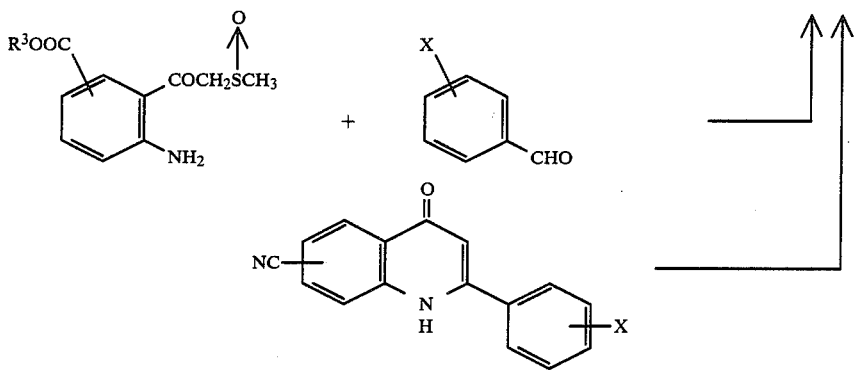

In the above formulae, $R^1$, $R^2$, $R^3$, $R^4$ and Z are as above defined.

The compounds of the present invention and their pharmaceutically acceptable salts may be formulated into pharmaceutical compositions using techniques per se known. Pharmaceutical compositions may thus be prepared which are useful for administration to humans and animals suffering from asthma, hay fever, hives, atopic dermatitis, inflammations such as that resulting from chronic articular rheumatism, post-operational pain, arthrosis deformans, low back pain, acute upper respiratory inflammation, toothache, dysmenorrhea. Such compositions may also be formualted for inhibition of platelet coagulation and are thus useful as anti-thrombotic agents. Such pharmaceutical compositions are produced by combining a therapeutically effective amount of a compound of the formula (I) or a pharmaceutically acceptable salt thereof with a pharmaceutically acceptable carrier.

The present invention also includes methods of effecting anti-inflammatory, anti-allergenic, expectorant and antitussive action and inhibiting coagulation of platelet aggregation in humans and animals which comprises administering a therapeutically effective amount of a compound of the formula (I) or a pharmaceutically acceptable salt thereof in combination with a pharmaceutically acceptable carrier.

Suitable pharmaceutical compositions according to the present invention may contain from 0.1% to 99% of a compound of the formula (I) or a pharmaceutically acceptable salt thereof or more preferably from about 0.5% to about 90%. Such pharmaceutical compositions are preferably in dosage unit form; i.e., physically discrete units containing a predetermined amount of the compound of the formula (I) or a pharmaceutically acceptable salt thereof corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day.

Although the dosage and dosage regimen must in each case be carefully adjusted, utilizing sound professional judgment and considering the age, weight and condition of the recipient, the route of administration and the nature and gravity of the illness, generally the dosage will be as follows: for oral administration from about 1 to about 1000 mg one to three times per day of said compound or salt thereof for an average adult. For parenteral administration and as eye drops, from about 0.1 to about 50 mg three to four times per day. For rectal administration, from about 1 to about 500 mg one to three times per day. For inhalation and nasal administration, from about 0.1 to about 100 mg two to three times per day. For topical application such as ointment, from about 1 to about 100 mg two to three times per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as, for example, starch or mannitol. Flavoring, preservative, dispersing, and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availablity of the medicament when the capsule is ingested.

Tablets are formulated, for example, by preparing a powder mixture, granulating or slugging, adding a lubricant and disintegrant and pressing into tablets. a powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the table forming dies by means of the addition of stearic acid, a stearate salt, talc or mineral oil. The lubricated mixture is then compressed into tablets. The compounds and pharmaceutically acceptable salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

The compositions and methods of the present invention are particularly useful for oral administration.

The compounds of the present invention have been evaluated for their anti-allergenic action by passive cutaneous anaphylatic assay (PCA) in rats and by measuring the anti-SRS-A action using ileus of guinea pigs.

Test method No. 1 (PCA)

(i) Antiserum abundant in homocytotropic antibody is prepared by the same method as Tada and Okumura did (cf. Journal of Immunology, vol. 106, page 1002, 1971). Thus, 1 mg (calculated as an amount of protein) of DNP-As (2,4-dinitrophenylcoupled ascaris extract) prepared by methods of Strejan and Campbell (Journal of Immunology, vol. 98, p. 893, 1967) and of Eisen (Journal of Amer. Chem. Soc., vol. 75, p 4593, 1953) and $1 \times 10^{10}$ pertussis vaccine are administered to each paw of Wistar strain rats (180 to 200 grams body weights) by dividing the dose by four. Five days later, 0.5 mg of DNP-As is administered into muscle of back. Eight days later from the initial immunization, blood is taken from discending aorta under anesthetizing with ether, the resulting serum is stored at $-80°$ and is melted before use.

(ii) Effect of tested compounds is investigated as follows:

Anti-serum obtained by th method (i) is diluted with physiological saline solution double by double successively and 0.05 ml of each diluted solution is administered into the back of Wistar strain rats (140 to 160 grams body weight) intradermally. After 72 hours, a solution of 2 mg (calculated as protein) of DNP-As and 2.5 mg of Evans Blue dissolved in 1 ml of physiological saline solution is administered intraveously at a dose of 5 ml/kg. After 30 minutes from the antigen solution administration, the animals are killed and the diameters of blue spots which appeared at the place where antiserum was administered were measured. The PCA test is conducted by the same method as already described using a diluted solutions of antiserum which always show 10 mm or more of spot diameters and the effect of the test compounds is judged. Thus antiserum diluted solutions are administered into two places in the back. Test compounds are administered orally at the dose of 10 mg/kg one hour before administration of the antigen solution. From the skin of reacted parts of killed animals, leaked or emitted dyestuff is extracted and the amount of the dyestuff is measured. The inhibition ratio is calculated by the following expression:

$$\text{Inhibition Ratio} = \left(1 - \frac{A'}{A}\right) \times 100$$

in which $A'$ is an amount of dyestuff in the group treated with the test compounds and $A$ is that in the control group.

Test Method No. 2

Anti-SRS-A action (An anti-acton against slow reacting substance of anaphylaxis).

Hartley strain male guinea pigs (300 to 350 grams body weight) are killed and 1.0 to 1.5 cm of ileum is immeidiately excised from ileocecal parts and is suspended in 10 ml of Tyrode solution (95% $O_2$–5% $CO_2$ saturation) containing $10^{-7}$ g/ml of atropine and $10^{-6}$ g/ml of pyrilamine. SRS-A (20 units) (the amount of SRS-A showing the same contradiction as 5 ng of histamine is defined as 1 unit) prepared by using sensitized guinea pig lung is given to cause contraction there. Then antagonistic action of test compounds treated five minutes ago against the contraction is measured and recorded via isotonic transducer.

$$\text{Inhibition Ratio of Test Compd (\%)} = \left(1 - \frac{A'}{A}\right) \times 100$$

in which $A'$ is a height of contraction of SRS-A+test compound and $A$ is that of SRS-A.

TABLE 1

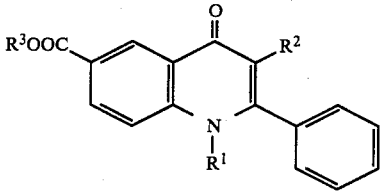

| R¹ | R² | R³ | PCA Inhibition Ratio % | 1/1000 mM SRS-A Inhibition Ratio % |
|---|---|---|---|---|
| H | H | H | 22.5 | 23.9 |
| H | H | Na salt | 27.9 | 85.0 |
| H | H | Methyl | 25.4 | 77.0 |
| H | H | Ethyl | 25.7 | 27.5 |
| H | H | iso-Propyl | 26.2 | 36.7 |
| H | H | Phenethyl | 24.3 | 22.8 |
| H | Methyl | H | 22.4 | 21.0 |
| H | Methyl | Methyl | 26.8 | 54.8 |
| H | Allyl | H | 17.5 | 22.3 |
| H | Allyl | Methyl | 20.1 | 37.5 |
| Methyl | H | H | 16.2 | 22.0 |
| Methyl | H | Methyl | 21.3 | 100 |
| Ethyl | H | H | 16.4 | 28.9 |
| Ethyl | H | Methyl | 18.9 | 25.4 |
| n-Propyl | H | H | 23.4 | 19.7 |
| n-Propyl | H | Methyl | 19.7 | 65.3 |
| Allyl | H | H | 26.5 | 24.3 |
| Allyl | H | Methyl | 20.4 | 22.7 |
| n-Hexyl | H | H | 26.4 | 83.9 |
| n-Hexyl | H | Methyl | 27 | 27.5 |

In the compounds set forth in the table below, Z is a phenyl moiety substituted by the substituents set forth in the table.

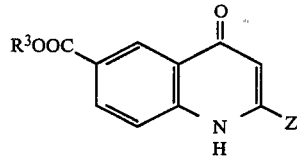

| Substituent on Phenyl | R³ | PCA Inhibition Ratio % | 1/1000mM SRS-A Inhibition Ratio % |
|---|---|---|---|
| 3-Chloro | Methyl | 7.8 | 48.3 |
| 2-Chloro | H | 35.8 | 26.4 |
| 2-Chloro | Na salt | 18.7 | 24.9 |
| 2-Bromo | Methyl | 23.4 | 55.8 |
| 2-Bromo | H | 17.2 | 25.7 |
| 2-Fluoro | Methyl | 20.6 | 38.5 |
| 2-Fluoro | H | 25.6 | 23.4 |
| 2-Iodo | Methyl | 19.6 | 55.6 |
| 3-Chloro | Methyl | 21.2 | 33.3 |
| 3-Chloro | H | 43.0 | 24.5 |
| 3-Chloro | Na salt | 24.4 | 25.5 |
| 4-Chloro | Methyl | 24.4 | 20.6 |
| 4-Chloro | H | 22.3 | 22.5 |
| 2,4-Dichloro | Methyl | 17.4 | 19.3 |
| 2,4-Dichloro | H | 39.4 | 25.6 |
| 2,4-Dichloro | Na salt | 20.4 | 14.5 |
| 3,4-Dichloro | Methyl | 17.1 | 24.3 |
| 3,4-Dichloro | H | 20.4 | 20.5 |
| 2,5-Dichloro | Methyl | 24.8 | 66.0 |
| 2,5-Dichloro | H | 25.4 | 27.5 |
| 2-Methyl | Methyl | 29.5 | 29.1 |
| 2-Methyl | H | 43.2 | 17.4 |
| 2-Methyl | Na salt | 24.8 | 17.3 |
| 2-Ethyl | Methyl | 18.0 | 41.3 |
| 2-Ethyl | H | 24.2 | 25.4 |
| 4-Methyl | Methyl | 27.3 | 19.8 |
| 4-Methyl | H | 17.3 | 18.9 |
| 4-Isopropyl | Methyl | 26.4 | 24.2 |
| 4-Isorpopyl | H | 25.2 | 18.8 |

-continued

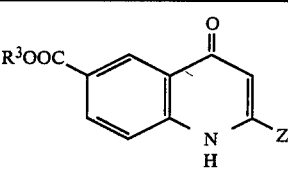

| Substituent on Phenyl | R³ | PCA Inhibition Ratio % | 1/1000mM SRS-A Inhibition Ratio % |
|---|---|---|---|
| 4-n-Pentyl | Methyl | 19.4 | 36.0 |
| 4-n-Pentyl | H | 22.7 | 61.4 |
| 3-Trifluoromethyl | Methyl | 25.0 | 21.3 |
| 3-Trifluoromethyl | H | 22.4 | 30.0 |
| 2,4-Dimethyl | Methyl | 18.9 | 22.4 |
| 2,4-Dimethyl | H | 16.8 | 17.5 |
| 2-Methoxy | Methyl | 22.3 | 25.2 |
| 2-Methoxy | H | 20.4 | 27.7 |
| 2-Ethoxy | Methyl | 23.1 | 63.0 |
| 2-Ethoxy | H | 15.8 | 24.6 |
| 2-Isopropoxy | Methyl | 21.2 | 58.8 |
| 2-Isopropoxy | H | 20.1 | 31.8 |
| 4-Methoxy | Methyl | 19.0 | 27.4 |
| 4-Methoxy | H | 18.4 | 23.0 |
| 2,4-Dimethoxy | Methyl | 17.7 | 48.2 |
| 2,4-Dimethoxy | H | 26.9 | 27.3 |
| 3,4-Dimethoxy | Methyl | 25.4 | 25.7 |
| 3,4-Dimethoxy | H | 17.4 | 25.0 |
| 4-Methoxycarbonyl | Methyl | 19.8 | 36.8 |
| 4-Carboxy | H | 25.8 | 27.9 |

In the compounds set forth below, Z is the heterocycle as specified:

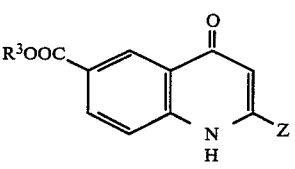

| (Z) | R³ | PCA Inhibition Ratio % | 1/1000mM SRS-A Inhibition Ratio % |
|---|---|---|---|
| 4-Pyridyl | Methyl | 22.3 | 21.4 |
| 4-Pyridyl | H | 25.6 | 25.0 |
| 3-Pyridyl | Methyl | 17.8 | 22.0 |
| 3-Pyridyl | H | 20.4 | 23.8 |
| 2-Pyridyl | Methyl | 23.1 | 25.0 |
| 2-Pyridyl | H | 20.4 | 28.9 |
| 2-Furyl | Methyl | 21.3 | 25.6 |
| 2-Furyl | H | 17.4 | 21.0 |
| 2-Thienyl | Methyl | 26.7 | 23.3 |
| 2-Thienyl | H | 19.8 | 19.5 |

In the compounds set forth below, Z is a phenyl moiety substituted by the substituents set forth in the table:

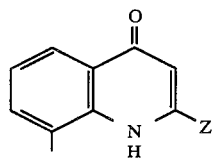

| (Z) | R³ | PCA Inhibition Ratio % | 1/1000mM SRS-A Inhibition Ratio % |
|---|---|---|---|
| H | H | 35.3 | 26.4 |
| H | Na salt | 10.0 | 27.3 |
| H | Ethyl | 20.9 | 52.4 |
| 2-Chloro | Ethyl | 28.5 | 75.9 |
| 2-Chloro | H | 17.0 | 27.9 |
| 2-Chloro | Methyl | 17.4 | 14.7 |
| 2-Chloro | n-Propyl | 2.4 | 7.8 |
| 2-Chloro | iso-Butyl | 24.3 | 25.0 |
| 2-Chloro | n-Hexyl | 10.5 | 20.5 |
| 2-Chloro | 2-Hydroxyethyl | 29.2 | 100 |
| 2-Chloro | 3-Hydroxypropyl | 12.4 | 27.4 |
| 2-Chloro | 5-Hydroxypropyl | 15.0 | 23.7 |
| 2-Chloro | 6-Hydroxyhexyl | 50.0 | 8.7 |
| 2-Chloro | allyl | 17.7 | 18.9 |
| 2-Chloro | 2-Acetyloxyethyl | 41.5 | 64.2 |
| 2-Chloro | 2-Phenoxyethyl | 47.0 | 73.4 |
| 2-Chloro | Ethoxyethyl | 10.7 | 20.3 |
| 2-Chloro | Cyanomethyl | 54.4 | 3.4 |
| 2-Chloro | 2-Oxopropyl | 14.7 | 20.4 |
| 2-Chloro | Ethoxycarbonylmethyl | 16.0 | 17.4 |
| 2-Chloro | 2-Hydroxypropyl | 10.4 | 15.6 |
| 2-Chloro | 2,3-Dihydroxypropyl | 15.3 | 19.2 |
| 2-Chloro | 2-Isobutoxyethyl | 13.3 | 25.4 |
| 2-Chloro | 2-(2-Hydroxyethoxy)ethyl | 10.7 | 25.0 |
| 2-Chloro | 2-(2-Ethoxyethoxy)ethyl | 5.4 | 10.2 |
| 2-Chloro | 2-Oxo-3-(ethoxycarbonyl)propyl | 20.3 | 12.7 |
| 2-Fluoro | Ethyl | 28.5 | 33.3 |
| 2-Fluoro | 2-Hydroxyethyl | 28.5 | 14.0 |
| 3-Chloro | Ethyl | 20.1 | 62.5 |
| 3-Chloro | H | 19.3 | 20.7 |
| 3-Chloro | 2-Hydroxyethyl | 18.6 | 55.5 |
| 4-Chloro | Ethyl | 14.7 | 12.4 |
| 4-Chloro | 2-Hydroxyethyl | 17.0 | 21.3 |
| 2,4-Dichloro | Ethyl | 26.2 | 55.6 |
| 2,4-Dichloro | H | 23.4 | 53.6 |
| 2,4-Dichloro | Methyl | 17.5 | 45.5 |
| 3,4-Dichloro | H | 22.7 | 24.2 |
| 2-Methyl | Ethyl | 10.4 | 19.8 |
| 2-Methyl | 2-Hydroxyethyl | 10.8 | 5.2 |
| 4-Methyl | Ethyl | 22.4 | 30.3 |
| 4-Methyl | H | 23.5 | 26.7 |
| 4-Methyl | 2-Hydroxyethyl | 35.0 | 27.3 |
| 2,4-Dimethyl | Ethyl | 25.7 | 78.6 |
| 2,4-Dimethyl | H | 24.2 | 22.8 |
| 2,4-Dimethyl | 2-Hydroxyethyl | 19.4 | 15.4 |
| 3,4-Dimethyl | Ethyl | 17.3 | 10.4 |
| 3,4-Dimethyl | 2-Hydroxyethyl | 20.0 | 10.8 |
| 4-Isopropyl | Ethyl | 33.4 | 44.0 |
| 4-n-Octyl | Ethyl | 21.5 | 23.8 |
| 4-n-Octyl | H | 22.0 | 33.7 |
| 4-Methoxy | Ethyl | 3.2 | 20.3 |
| 4-Methoxy | 2-Hydroxyethyl | 12.7 | 25.4 |
| 2,4-Dimethoxy | Ethyl | 14.0 | 95.0 |
| 2,4-Dimethoxy | 2-Hydroxyethyl | 18.4 | 63.3 |
| 3,4-Dimethoxy | Ethyl | 16.4 | 20.4 |
| 3,4-Dimethoxy | H | 13.2 | 21.7 |
| 3,4-Dimethoxy | 2-Hydroxyethyl | 19.4 | 18.3 |

-continued

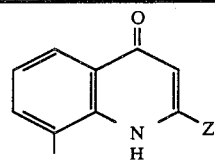

| (Z) | R³ | PCA Inhibition Ratio % | 1/1000mM SRS-A Inhibition Ratio % |
|---|---|---|---|
| | OH | 29.7 | 70.5 |

[structure: 4-hydroxyquinoline with 8-COOEt and 2-(2-chlorophenyl)·HCl]

The anti-inflammatory action of the compounds of the present invention were evaluated by measuring the inhibition against carrageenin edema as set forth below.

Carrageenin edema at the hind foot of rats:
Experimental method.

SD-strain rats of body weights of around 150 grams were used, each group consisting of five rats. A solution (0.1 ml) of 0.5% carrageenin dissolved in physiological saline water was subcutaneously injected into the right hind foot pat of the rats and, one hour prior to the injection of carrageenin, 200 mg/kg of test compound was given per os. Foot volumes of the rats before the carrageenin treatment and those of three hours after the treatment were measured and the differences were compared with those of the control group to adopt as a target of the effect of the compounds.

Results of the representative compounds are as follows:

| Example Numbers | % Inhibition |
|---|---|
| 20 | 10.6 |
| 4 | 14.2 |
| 41 | 18.9 |
| 42 | 11.8 |
| 22 | 14.8 |
| 38 | 12.8 |
| 28 | 15.9 |
| 70 | 17.1 |
| 64 | 10.1 |
| 39 | 30.0 |
| 83 | 22.5 |
| 86 | 29.5 |
| 76 | 14.5 |
| 70 | 15.0 |
| 99 | 36.8 |
| 80 | 14.7 |
| 109 | 30.7 |
| 124 | 14.5 |
| 120 | 29.4 |
| 112 | 10.0 |
| 130 | 18.3 |
| 125 | 17.2 |
| 106 | 50.9 |
| 102 | 56.5 |
| 108 | 51.0 |
| 118 | 27.9 |
| 136 | 26.9 |
| 110 | 19.2 |
| 133 | 10.0 |
| 131 | 29.9 |
| 104 | 53.7 |
| 98 | 16.1 |

-continued

| Example Numbers | % Inhibition |
|---|---|
| 1 | 34.0 |
| (Control: Acetylsalicylic Acid | 31.6) |

Action against Platelet Coagulation was determined as follows:

Male rabbits with body weights of 3 kg or around 10 were used. Blood was taken from their carotid artery and, immediately thereafter, 1/10 volume (to the blood) of 3.8% aqueous solution of sodium citrate was added thereto. The mixture was centrifuged at room temperature (400 g; 10 minutes) to give platelet rich plasma (abbreviated as PRP: containing $5 \times 10^5$ platelets per $mm^3$). The PRP was then placed into a cell for platelet coagulation meter (Niko Bioscience), stirred, 5 microliters of test compound solution in dimethyl sulfoxide was added and, one minute thereafter, 5 micromolar of ADP, 10 micrograms/ml of collagen or 25 microliters of arachidoic acid (AA) was added thereto to observe changes of extinctions.

From the maximum coagulation value at the time of administration the of test compound against that at the time of the solvent addition, inhibition was calculated and the effect of the compounds against the platelet coagulation was determined.

TABLE 2

Effect of the present invention compounds and indomethacin on platelet aggregation induced by ADP, collagen and AA in platelet rich plasma of rabbits

| Name of Compound | Final Concentration (M) | Inhibition (%) | | |
|---|---|---|---|---|
| | | ADP (5 μM) | Collagen (10 μg/ml) | AA (150 μM) |
| Example 83 | $10^{-5}$ | — | 14.0 | 3.3 |
| | $10^{-4}$ | 18.5 | 100.0 | 100 |
| Indomethacin | $10^{-6}$ | — | 19.6 | 1.6 |
| | $10^{-5}$ | — | 100.0 | 100.0 |
| | $10^{-4}$ | 2.6 | 100.0 | 100.0 |

Acute toxicity was determined two weeks after oral administration of 4000 mg/kg to male mice. Four mice (denominator) are used in each group and the dead numbers are given as the numerator. The compounds of the present invention show little, if any, toxicity. Representative examples are given in Table 2.

TABLE 2

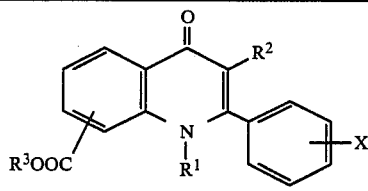

| Example No. | $R^1$ | $R^2$ | $R^3$ | X | Lethal Ratio |
|---|---|---|---|---|---|
| 20 | n-$C_6H_{13}$ | H | (6-position) H | H | ½ |
| 28 | H | H | (6-position) $CH_3$ | 2'-I | 0/4 |
| 42 | H | H | (6-position) H | 2'-$CH_3$ | 0/4 |
| 56 | H | H | (6-position) $CH_3$ | 2'-$OCH_3$ | ½ |
| 83 | H | H | (8-position) $C_2H_5$ | 2'-Cl | 0/4 |
| 84 | H | H | (8-position) Na | 2'-Cl | 0/4 |
| 85 | H | H | (8-position) H | 2'-Cl | 0/4 |
| 89 | H | H | (8-position) $C_2H_5$ | 2',4'-$Cl_2$ | 0/4 |
| 94 | H | H | (8-position) $C_2H_5$ | 2',4'-$(CH_3)_2$ | ½ |

TABLE 2-continued

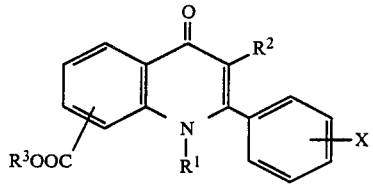

| Example No. | $R^1$ | $R^2$ | $R^3$ | X | Lethal Ratio |
|---|---|---|---|---|---|
| 100 | H | H | (8-position) $C_2H_5$ | 2'-Cl | 0/4 |

Lethal ratios for all other compounds are 0/4 at doses of 2000 mg/kg. It is therefore apparent that they are all safe compounds.

The following non-limitative examples more particularly illustrate the compounds of the present invention and the formulation of various pharmaceutical preparations.

REFERENCE EXAMPLE 1

Ethyl o-chlorobenzoylacetate

Sodium hydride (8.7 grams) and 21.4 grams of diethyl carbonate are suspended in 100 ml of tetrahydrofuran, 14 grams of o-chloroacetophenone is gradually dropped thereinto by keeping the inner temperature at 40° to 50° C., then a small amount of ethanol is added thereto and heated to reflux for four hours. After cooling, 20 ml of ethanol is added thereto, the mixture is poured into ice water, and extracted with ether. Ether extracts are combined, washed with water, dried with anhydrous magnesium sulfate, and ether is evaporated therefrom. The resulting oil is purified by distillation in vacuo to give 8.8 grams of colorless, oily product, b.p. 120° to 125° C./1 mmg Hg.

REFERENCE EXAMPLE 2

Ethyl p-isopropylbenzoylacetate

Sodium hydride (2.4 grams) and 4.5 grams of dimethyl carbonate are suspended in 150 ml of ether. 8.1 grams of p-isopropylacetophenone is gradually dropped thereinto under heating to reflux, then a small amount of ethanol is added thereto, heated to reflux for one hour, cooled, and the reaction is stopped by the addition of 20 ml of ethanol. The mixture is poured into ice water and extracted with ether. The ether extracts are combined, washed with water, dried with anhydrous magnesium sulfate and ether is evaporated therefrom. The resulting oil is purified by distillting in vacuo to give 6.5 grams of colorless oily product, b.p. 80° C./5 mmHg.

REFERENCE EXAMPLE 3

Ethyl 2-furoylacetate

Sodium hydride (4.4 grams) and 10.7 grams of diethyl carbonate are suspended in 60 ml of tetrahydrofuran and 10 grams of 2-acetylfuran is gradually added thereto by keeping the inner temperature at 40°to 50° C. A small amount of ethanol is added thereto, heated to reflux for three hours, and the reaction is made stopped by addition of 20 ml of ethanol. The mixture is poured into ice water, extracted with ether, the ether extracts are combined, washed with water, dried with anhydrous magnesium sulfate, and ether is evaporated therefrom. The resulting oil is purified by distilling in vacuo to give 10 grams of pale yellow oily product, b.p. 90° C./3 mmHg.

REFERENCE EXAMPLE 4

Ethyl m-trifluoromethylbenzolacetate

Cyclohexyl isopropylamine (16.4 grams) is dissolved in 100 ml of tetrahydrofuran and the solution is cooled at −78° C. In a nitrogen atmosphere, 40 ml of about 15% n-butyl lithium solution in hexane is added thereto. The mixture temperature is raised up to −40° C. during thirty minutes. Then it is cooled to −78° C. again and 4.5 grams of ethyl acetate is added thereto during five minutes. Then, after ten minutes, a solution of 12.1 grams of m-trifluoromethylbenzoic acid chloride in tetrahydrofuran is dropped thereinto gradually. The mixture is stirred at −78° C. for one hour then raised to 0° C. during two hours. To this is added 20 ml of 20% hydrochloric acid solution, the mixture is poured into ice water, and extracted with ether. The extract is washed with saturated aqueous solution of sodium bicarbonate, dried with anhydrous magnesium sulfate, ether is evaporated therefrom, and the resulting oil is purified by distilling in vacuo to give 10.7 grams of pale yellow oil, b.p. 125° to 130° C./5 mmHg.

REFERENCE EXAMPLE 5

Ethyl o-iodobenzoylacetate

Cyclohexyl isopropylamine (10.6 grams) is dissolved in 80 ml of tetrahydrofuran and the solution is cooled to −78° C. In a nitrogen stream, a solution of n-butyl lithium (about 15%) in hexane solution (26 ml) is added thereto, and the mixture temperature is raised to −40° C. Then it is cooled to −78° C. once again, 3.3 grams of ethyl acetate is gradually added thereto and, ten minutes thereafter, a solution of 10 grams of o-iodobenzoyl chloride in tetrahydrofuran is dropped thereinto gradually. The mixture is stirred at −78° C. for one hour, then gradually warmed up to 0° C. within two to three hours, 20 ml of 20% hydrochloric acid solution is added thereto, the mixture is poured into ice water, and extracted with ether. The extract is washed with a saturated aqueous solution of sodium bicarbonate, dried with anhydrous magnesium sulfate, ether is evaporated therefrom, and the resulting oil is purified by distilling in vacuo to give 8.5 grams of pale yellow oil, b.p. 142° C./3 mmHg.

REFERENCE EXAMPLE 6

Ethyl alpha-allylbenzoylacetate

Ethyl benzoylacetate (6 grams) is dissolved in 40 ml of dimethyl formamide and 1.5 grams of sodium hydride is added thereto with ice cooling and stirring. Ten minutes thereafter, 4 grams of allyl bromide is added thereto, the mixture is stirred at room temperature for one hour, and poured into water. The mixture is neutralized with acetic acid, and extracted with ether. The ether extract is washed with water, dried with anhydrous magnesium sulfate, and ether is evaporated therefrom to give 6.1 grams of colorless oily product.

EXAMPLE 1

Methyl 2-phenyl-4-quinolone-6-carboxylate

Methyl p-aminobenzoate (3.0 grams) and 4.1 grams of ethyl benzoylacetate are dissolved in 100 ml of chloroform and the solution is subjected to azeotropic dehydration for two days after the addition of 0.5 gram of p-toluenesulfonic acid. Chloroform is evaporated therefrom, n-hexane is added to the residue, the extract with n-hexane is evaporated, 30 ml of diphenyl ether is added to the residue, the mixture is heated at 255° C. for twenty minutes, cooled, crystals separate out therefrom are collected by filtration, washed with n-hexane and dried to give 4.4 grams of methyl 2-phenyl-4-quinolone-6-carboxylate, needles, melting at higher than 300° C.

Elementary analysis calculated as $C_{17}H_{13}NO_3$: C 73.11, H 4.69, N 5.02; Found: C 73.33, H 4.45, N 5.05.

EXAMPLE 2

2-Phenyl-4-quinolone-6-carboxylic acid

Methyl 2-phenyl-4-quinolone-6-carboxylate (3.8 grams) obtained in Example 1 is refluxed for three hours in a mixture of 100 ml of methanol, 3 grams of sodium hydroxide and 15 ml of water. The mixture is evaporated to dryness in vacuo, 100 ml of water is added to the residue, filtered, acidified with 10% hydrochloric acid solution, and the crystals which separate out therefrom are collected by filtration. These are recrystallized from dimethyl formamide to give 2.8 grams of 2-phenyl-4-quinolone-6-carboxylic acid, colorless powder, melting at above 300° C.

Elementary analysis calculated for $C_{16}H_{11}NO_3$: C 72.44, H 4.18, N 5.28; Found: C 72.44, H 3.89, N 5.22.

EXAMPLE 3

Sodium 2-phenyl-4-quinolone-6-carboxylate

2-Phenyl-4-quinolone-6-carboxylic acid (2.5 grams) obtained in Example 2 is dissolved, together with 0.8 gram of sodium hydroxide, in 50 ml of water and heated solution is concentrated, diluted with ethanol, and the crystals which separate out therefrom are collected by filtration. These are dried by heating to give 2.2 grams of sodium salt of 2-phenyl-4-quinolone-6-carboxylic acid, colorless powder, melting at above 300° C.

Elementary analysis calculated for $C_{16}H_{10}NO_3Na$: C 66.89, H 3.52, N 4.88; Found: C 66.67, H 3.74, N 4.77.

EXAMPLE 4

Ethyl 2-phenyl-4-quinolone-6-carboxylate

2-Phenyl-4-quinolone-6-carboxylic acid (1.3 grams) obtained in Example 2 is dissolved in 80 ml of ethanol and 0.5 ml of concentrated sulfuric acid. The solution is stirred for three days at 80° C., water is added thereto, crystals which separate out therefrom are collected by filtration. These are washed with water and dried to give 1.4 grams of ethyl 2-phenyl-4-quinolone-6-carboxylate, colorless powder, melting at above 300° C.

Elementary analysis calculated for $C_{18}H_{15}NO_3$: C 73.70, H 5.15, N 4.78; Found: C 73.52, H 5.30, N 4.76.

EXAMPLE 5

Isopropyl 2-phenyl-4-quinolone-6-carboxylate

Metal sodium (0.33 gram) is dissolved in 40 ml of anhydrous isopropyl alcohol and the solution is heated to reflux for one hour with 2 grams of the 2-phenyl-4-quinolone-6-carboxylic acid obtained in Example 2. After cooling, the solution is mixed with ice water, acidified with acetic acid, the crystals which separate out therefrom are collected by filtration. The crystals are washed with water, washed with methanol, and dried to give 0.6 gram of isopropyl 2-phenyl-4-quinolone-6-carboxylate, colorless powder, melting at above 300° C.

Elementary analysis calculated for $C_{19}H_{17}NO_3$: C 74.25, H 5.58, N 4.56; Found: C 73.99, H 54.6, N 4.31.

EXAMPLE 6

Phenethyl 2-phenyl-4-quinolone-6-carboxylate

2-Phenyl-4-quinolone-6-carboxylic acid (1.5 grams) obtained in Example 2 is stirred for fifteen hours at 110° C. with 50 ml of phenethyl alcohol and 1 ml of concentrated sulfuric acid. After cooling, 1.5 liters of ether is added to the mixture, the mixture is cooled with ice, oil which separates out therefrom is taken out. The mixture is then dissolved in 5 ml of ethanol. Then 3 ml of water is added thereto, and crystal which separates out therefrom are collected by filtration, and washed with a 5% sodium bicarbonate solution, then with water, and finally with methanol, and dried to give 0.9 gram of phenethyl 2-phenyl-4-quinolone-6-carboxylate, colorless powder, melting point 282° to 284° C.

Elementary analysis calculated for $C_{24}H_{19}NO_3$: C 78.03, H 5.18, N 3.79; Found: C 77.80, H 5.27, N 3.64.

EXAMPLE 7

Methyl 1-methyl-2-phenyl-4-quinolone-6-carboxylate

A mixture of 2 grams of methyl 2-phenyl-4-quinolone-6-carboxylate (obtained in Example 1), 16 ml of methyl iodide, 2 grams of potassium carbonate and 50 ml of dimethyl formamide is stirred for four hours at 60° C. After cooling, the mixture is poured into water and extracted with ethyl acetate. From the extract ethylacetate is evaporated, the residue is purified by silica chromatography, and 1.8 grams of methyl 1-methyl-2-phenyl-4-quinolone-6-carboxylate, colorless powder, melting point 174° to 176° C., is obtained.

Elementary analysis calculated for $C_{18}H_{15}NO_3$: C 73.70, H 5.15, N 4.78; Found: C 74.84, H 4.96, N 4.71.

EXAMPLE 8

1-Methyl-2-phenyl-4-quinolone-6-carboxylic acid.

To 0.9 gram of methyl 1-methyl-2-phenyl-4-quinolone-6-carboxylate obtained in Example 7 are added 0.5 gram of sodium hydroxide and 40 ml of water and the mixture is stirred at 60° C. for two hours. The mixture is acidified with acetic acid, and crystals which separate out therefrom are collected by filtration, and dried to give 0.5 gram of 1-methyl-2-phenyl-4-quinolone-6-carboxylic acid, colorless powder, melting at above 30° C.

Elementary analysis calculated for $C_{17}H_{13}NO_3$: C 73.11, H 4.69, N 5.02; Found: C 73.18, H 4.44, N 4.85.

EXAMPLE 9

Methyl 3-methyl-2-phenyl-4-quinolone-6-carboxylate

Ethyl alpha-methylbenzoylacetate (5 grams) and 3.67 grams of methyl p-aminobenzoate are dehydrated (by heating) for three days in 100 ml of chloroform in the presence of 0.7 gram of p-toluenesulfonic acid. p-Toluenesulfonic acid is removed therefrom, the filtrate is concentrated, and purified by silica gel column chromatography to give an oil. The resulting oily product is heated to reflux in 70 ml of diphenyl ether, cooled, and crystals which separate therefrom are collected by filtration and recrystallized from a mixture of dimethyl formamide and water to give 2 grams of methyl 3-methyl-2-phenyl-4-quinolone-6-carboxylate, colorless crystals, melting point above 300° C.

Elementary analysis calculated for $C_{18}H_{15}NO_3$: C 73.70, H 5.15, N 4.78; Found: C 73.84, H 5.03, N 4.86.

The compounds set forth in the table below may be produced by analagous procedures or in a manner analagous to the example illustrating the compound of example 57 set forth below.

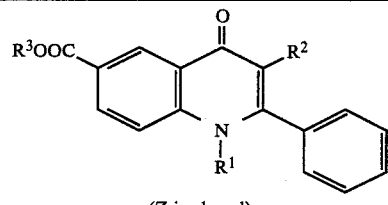

(Z is phenyl)

| Example No. | $R^1$ | $R^2$ | $R^3$ | Appearance | M.p. | Elementary Analysis | | |
|---|---|---|---|---|---|---|---|---|
| 10 | H | Me | H | Colorless Crystals | >300° C. | $C_{17}H_{13}NO_3$ | | |
| | | | | | | Calc'd (%) | C 73.11 H 4.69 | N 5.02 |
| | | | | | | Found (%) | C 73.05 H 4.47 | N 4.98 |
| 11 | H | $CH_2CH=CH_2$ | Me | Colorless Crystals | 235–236° C. | $C_{20}H_{17}NO_3$ | | |
| | | | | | | Calc'd (%) | C 75.22 H 5.37 | N 4.39 |
| | | | | | | Found (%) | C 75.13 H 5.59 | N 4.44 |
| 12 | H | $CH_2CH=CH_2$ | H | Colorless Crystals | >300° C. | $C_{19}H_{15}NO_3$ | | |
| | | | | | | Calc'd (%) | C 74.74 H 4.95 | N 4.59 |
| | | | | | | Found (%) | C 74.79 H 4.72 | N 4.55 |
| 13 | Et | H | Me | Colorless Powder | 152–155° C. | $C_{19}H_{17}NO_3$ | | |
| | | | | | | Calc'd (%) | C 74.25 H 5.58 | N 4.56 |
| | | | | | | Found (%) | C 74.42 H 5.49 | N 4.60 |
| 14 | Et | H | H | Colorless Crystals | >300° C. | $C_{18}H_{15}NO_3$ | | |
| | | | | | | Calc'd (%) | C 73.70 H 5.15 | N 4.78 |
| | | | | | | Found (%) | C 73.96 H 4.87 | N 4.84 |
| 15 | n-$C_3H_7$ | H | Me | Colorless Crystals | 133–136° C. | $C_{20}H_{17}NO_3$ | | |
| | | | | | | Calc'd (%) | C 74.74 H 5.96 | N 4.36 |
| | | | | | | Found (%) | C 74.65 H 5.93 | N 4.24 |
| 16 | n-$C_3H_7$ | H | H | Colorless Crystals | 223–225° C. | $C_{19}H_{17}NO_3$ | | |
| | | | | | | Calc'd (%) | C 74.25 H 5.58 | N 4.56 |
| | | | | | | Found (%) | C 74.22 H 5.62 | N 4.64 |
| 17 | $CH_2CH=CH_2$ | H | Me | Colorless Crystals | 147–149° C. | $C_{20}H_{17}NO_3$ | | |
| | | | | | | Calc'd (%) | C 75.22 H 5.37 | N 4.39 |
| | | | | | | Found (%) | C 75.05 H 5.31 | N 4.37 |
| 18 | $CH_2CH=CH_2$ | H | H | Colorless Crystals | 211–213° C. | $C_{19}H_{15}NO_3$ | | |

-continued

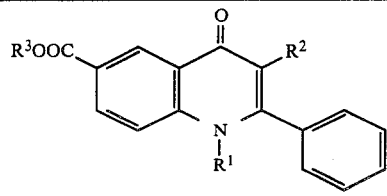

(Z is phenyl)

| Example No. | R¹ | R² | R³ | Appearance | M.p. | Elementary Analysis | | |
|---|---|---|---|---|---|---|---|---|
| 19 | n-$C_6H_{13}$ | H | Me | Colorless Crystals | 105–107° C. | Calc'd (%) C 74.74 H 4.95 N 4<br>Found (%) C 74.82 H 4.79 N 4<br>$C_{23}H_{25}NO_3$ | | |
| 20 | n-$C_6H_{13}$ | H | H | Colorless Crystals | 196–198° C. | Calc'd (%) C 76.00 H 6.93 N 3<br>Found (%) C 76.05 H 7.13 N 3<br>$C_{22}H_{23}NO_3$<br>Calc'd (%) C 75.62 H 6.63 N 4<br>Found (%) C 75.35 H 6.67 N 4 | | |

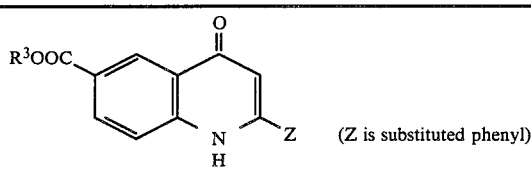

(Z is substituted phenyl)

| Example No. | Substituent(s) on phenyl | R³ | Appearance | M.p. | Elementary Analysis | | | |
|---|---|---|---|---|---|---|---|---|
| 21 | 2'-Cl | Me | Colorless needles | >300° C. | Calc'd (%)<br>Found (%) | $C_{17}H_{12}ClNO_3$<br>C 65.07 H 3.86 N 4.47<br>C 65.30 H 3.68 N 4.26 | | |
| 22 | 2'-Cl | H | Colorless powder | >300° C. | Calc'd (%)<br>Found (%) | $C_{16}H_{10}ClNO_3$<br>C 64.12 H 3.36 N 4.67<br>C 63.88 H 3.28 N 4.69 | | |
| 23 | 2'-Cl | Na | Colorless powder | >300° C. | Calc'd (%)<br>Found (%) | $C_{16}H_9ClNO_3Na$<br>C 52.34 H 3.81 N 3.81<br>C 52.62 H 3.53 N 3.73 | | |
| 24 | 2'-Br | Me | Pale yellow needles | 294–295° C. | Calc'd (%)<br>Found (%) | $C_{17}H_{12}BrNO_3$<br>C 57.00 H 3.38 N 3.91<br>C 57.13 H 3.20 N 3.82 | | |
| 25 | 2'-Br | H | Colorless powder | >300° C. | Calc'd (%)<br>Found (%) | $C_{16}H_{10}BrNO_3$<br>C 55.84 H 2.93 N 4.07<br>C 55.89 H 2.77 N 3.90 | | |
| 26 | 2'-F | Me | Colorless crystals | >300° C. | Calc'd (%)<br>Found (%) | $C_{17}H_{12}FNO_3$<br>C 68.68 H 4.09 N 4.71<br>C 68.69 H 3.81 N 4.67 | | |
| 27 | 2'-F | H | Colorless powder | >300° C. | Calc'd (%)<br>Found (%) | $C_{16}H_{10}FNO_3$<br>C 67.84 H 3.59 N 4.94<br>C 67.71 H 3.29 N 4.87 | | |
| 28 | 2'-I | Me | Pale yellow needles | >300° C. | Calc'd (%)<br>Found (%) | $C_{17}H_{12}INO_3$<br>C 50.39 H 2.99 N 3.46<br>C 50.45 H 3.01 N 3.24 | | |
| 29 | 3'-Cl | Me | Colorless needles | >300° C. | Calc'd (%)<br>Found (%) | $C_{17}H_{12}ClNO_3$<br>C 65.07 H 3.86 N 4.47<br>C 65.26 H 3.62 N 4.42 | | |
| 30 | 3'-Cl | H | Colorless powder | >300° C. | Calc'd (%)<br>Found (%) | $C_{16}H_{10}ClNO_3$<br>C 64.12 H 3.36 N 4.67<br>C 63.96 H 3.19 N 4.67 | | |
| 31 | 3'-Cl | Na | Colorless powder | >300° C. | Calc'd (%)<br>Found (%) | $C_{16}H_9ClNO_3Na$<br>C 53.67 H 3.63 N 3.91<br>C 53.44 H 3.41 N 3.82 | | |
| 32 | 4'-Cl | Me | Pale blue needles | >300° C. | Calc'd (%)<br>Found (%) | $C_{17}H_{12}ClNO_3$<br>C 65.07 H 3.86 N 4.47<br>C 65.29 H 3.64 N 4.34 | | |
| 33 | 4'-Cl | H | Colorless powder | >300° C. | Calc'd (%)<br>Found (%) | $C_{16}H_{10}ClNO_3$<br>C 64.12 H 3.36 N 4.67<br>C 63.94 H 3.10 N 4.49 | | |
| 34 | 2',4'-$Cl_2$ | Me | Colorless crystals | >300° C. | Calc'd (%)<br>Found (%) | $C_{17}H_{11}Cl_2NO_3$<br>C 58.64 H 3.18 N 4.02<br>C 58.91 H 2.95 N 3.88 | | |
| 35 | 2',4'-$Cl_2$ | H | Colorless powder | >300° C. | Calc'd (%)<br>Found (%) | $C_{16}H_9Cl_2NO_3$<br>C 57.51 H 2.71 N 4.19<br>C 57.68 H 2.47 N 3.98 | | |
| 36 | 2',4'-$Cl_2$ | Na | Colorless powder | >300° C. | Calc'd (%) | $C_{16}H_8Cl_2NO_3Na$<br>C 53.67 H 3.63 N 3.91 | | |

-continued

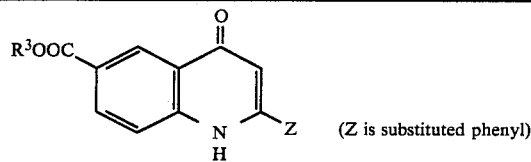

(Z is substituted phenyl)

| Example No. | Substituent(s) on phenyl | R³ | Appearance | M.p. | Elementary Analysis |
|---|---|---|---|---|---|
| 37 | 3',4'-Cl₂ | Me | Colorless needles | >300° C. | $C_{17}H_{11}Cl_2NO_3$<br>Calc'd (%) C 58.64  H 3.18  N 4.02<br>Found (%) C 58.90  H 2.96  N 3.85 |
| 38 | 3',4'-Cl₂ | H | Colorless powder | >300° C. | $C_{16}H_9Cl_2NO_3$<br>Calc'd (%) C 57.46  H 2.69  N 4.19<br>Found (%) C 57.51  H 2.45  N 4.09 |
| 39 | 2',5'-Cl₂ | Me | Colorless powder | >300° C. | $C_{17}H_{11}Cl_2NO_3$<br>Calc'd (%) C 58.64  H 3.18  N 4.02<br>Found (%) C 58.88  H 3.15  N 3.94 |
| 40 | 2',5'-Cl₂ | H | Colorless powder | >300° C. | $C_{16}H_9Cl_2NO_3$<br>Calc'd (%) C 57.46  H 2.69  N 4.19<br>Found (%) C 57.40  H 2.93  N 4.37 |
| 41 | 2'-Me | Me | Colorless powder | >300° C. | $C_{18}H_{15}NO_3$<br>Calc'd (%) C 73.70  H 5.15  N 4.78<br>Found (%) C 73.67  H 5.07  N 4.99 |
| 42 | 2'-Me | H | Colorless powder | >300° C. | $C_{17}H_{13}NO_3$<br>Calc'd (%) C 73.11  H 4.69  N 5.02<br>Found (%) C 73.23  H 4.60  N 5.18 |
| 43 | 2'-Me | Na | Colorless powder | >300° C. | $C_{17}H_{12}NO_3Na$<br>Calc'd (%) C 62.15  H 4.56  N 4.26<br>Found (%) C 61.98  H 4.61  N 4.12 |
| 44 | 2'-Et | Me | Colorless powder | 249–251° C. | $C_{17}H_{12}NO_3$<br>Calc'd (%) C 74.25  H 5.58  N 4.56<br>Found (%) C 74.23  H 5.30  N 4.55 |
| 45 | 2'-Et | H | Colorless powder | >300° C. | $C_{18}H_{15}NO_3$<br>Calc'd (%) C 73.70  H 5.15  N 4.78<br>Found (%) C 73.69  H 5.19  N 4.73 |
| 46 | 4'-Et | Me | Colorless crystals | >300° C. | $C_{18}H_{15}NO_3$<br>Calc'd (%) C 73.70  H 5.15  N 4.78<br>Found (%) C 73.90  H 5.05  N 4.75 |
| 47 | 4'-Me | H | Colorless powder | >300° C. | $C_{17}H_{13}NO_3$<br>Calc'd (%) C 73.11  H 4.69  N 5.02<br>Found (%) C 73.30  H 4.61  N 4.96 |
| 48 | 4'-isoC₃H₇ | Me | Colorless powder | >300° C. | $C_{10}H_{19}NO_3$<br>Calc'd (%) C 74.74  H 5.96  N 4.36<br>Found (%) C 75.00  H 5.89  N 4.40 |
| 49 | 4'-isoC₃H₇ | H | Colorless powder | >300° C. | $C_{19}H_{17}NO_3$<br>Calc'd (%) C 74.25  H 5.58  N 4.56<br>Found (%) C 74.11  H 5.42  N 4.61 |
| 50 | 4'-n-C₅H₁₁ | Me | Colorless powder | >300° C. | $C_{22}H_{23}NO_3$<br>Calc'd (%) C 75.62  H 6.63  N 4.01<br>Found (%) C 75.76  H 6.72  N 4.14 |
| 51 | 4'-n-C₅H₁₁ | H | Colorless powder | >300° C. | $C_{17}H_{21}NO_3$<br>Calc'd (%) C 75.20  H 6.31  N 4.18<br>Found (%) C 75.19  H 6.32  N 4.21 |
| 52 | 3'-CF₃ | Me | Colorless powder | >300° C. | $C_{18}H_{12}F_3NO_3$<br>Calc'd (%) C 62.25  H 3.48  N 4.03<br>Found (%) C 62.48  H 3.37  N 3.92 |
| 53 | 3'-CF₃ | H | Colorless powder | >300° C. | $C_{17}H_{10}F_3NO_3$<br>Calc'd (%) C 61.27  H 3.02  N 4.20<br>Found (%) C 61.23  H 2.90  N 4.38 |
| 54 | 2',4'-(Me)₂ | Me | Colorless needles | >300° C. | $C_{19}H_{17}NO_3$<br>Calc'd (%) C 74.25  H 5.58  N 4.56<br>Found (%) C 74.50  H 5.34  N 4.40 |
| 55 | 2',4'-(Me)₂ | H | Colorless powder | >300° C. | $C_{18}H_{15}NO_3$<br>Calc'd (%) C 73.70  H 5.15  N 4.78<br>Found (%) C 73.57  H 4.93  N 4.81 |
| 56 | 2'-OMe | Me | Colorless powder | 277–278° C. | $C_{18}H_{15}NO_4$<br>Calc'd (%) C 69.89  H 4.89  N 4.53<br>Found (%) C 70.05  H 4.76  N 4.39 |
| 57 | 2'-OMe | H | Colorless powder | 290–294° C. | $C_{17}H_{13}NO_4 \cdot H_2O$<br>Calc'd (%) C 65.17  H 4.70  N 4.44<br>Found (%) C 65.11  H 4.53  N 4.34 |
| 58 | 2'-OEt | Me | Colorless needles | 244–245° C. | $C_{19}H_{17}NO_4$<br>Calc'd (%) C 70.57  H 5.30  N 4.33<br>Found (%) C 70.78  H 5.31  N 4.35 |
| 59 | 2'-OEt | H | Colorless prisms | >300° C. | $C_{18}H_{15}NO_4$<br>Calc'd (%) C 69.89  H 4.89  N 4.53<br>Found (%) C 70.02  H 4.83  N 4.55 |
| 60 | 2'-O—isoC₃H₇ | Me | Colorless | 255– | $C_{20}H_{19}NO_4$ |

-continued

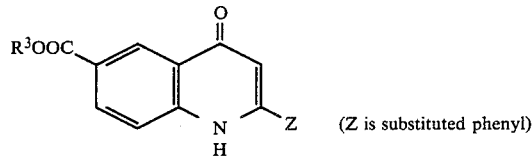
(Z is substituted phenyl)

| Example No. | Substituent(s) on phenyl | R³ | Appearance | M.p. | Elementary Analysis | | | |
|---|---|---|---|---|---|---|---|---|
|  |  |  | crystals | 256° C. | Calc'd (%) | C 71.20 | H 5.68 | N 4.15 |
|  |  |  |  |  | Found (%) | C 71.19 | H 5.66 | N 4.10 |
| 61 | 2'-O—isoC₃H₇ | H | Colorless powder | >300° C. |  | C₁₉H₁₇NO₄ | | |
|  |  |  |  |  | Calc'd (%) | C 70.57 | H 5.30 | N 4.33 |
|  |  |  |  |  | Found (%) | C 70.70 | H 5.20 | N 4.28 |
| 62 | 4'-OMe | Me | Colorless needles | >300° C. |  | C₁₈H₁₅NO₄ | | |
|  |  |  |  |  | Calc'd (%) | C 69.89 | H 4.89 | N 4.53 |
|  |  |  |  |  | Found (%) | C 70.00 | H 4.73 | N 4.49 |
| 63 | 4'-OMe | H | Colorless needles | >300° C. |  | C₁₇H₁₃NO₄·½H₂O | | |
|  |  |  |  |  | Calc'd (%) | C 67.10 | H 4.60 | N 4.60 |
|  |  |  |  |  | Found (%) | C 67.37 | H 4.30 | N 4.52 |
| 64 | 2',4'-(OMe)₂ | Me | Colorless crystals | 272–273° C. |  | C₁₉H₁₇NO₅ | | |
|  |  |  |  |  | Calc'd (%) | C 67.25 | H 5.05 | N 4.13 |
|  |  |  |  |  | Found (%) | C 66.94 | H 5.11 | N 3.94 |
| 65 | 2',4'-(OMe)₂ | H | Pale yellow powder | >300° C. |  | C₁₈H₁₅NO₅ | | |
|  |  |  |  |  | Calc'd (%) | C 66.45 | H 4.65 | N 4.31 |
|  |  |  |  |  | Found (%) | C 66.53 | H 4.55 | N 4.24 |
| 66 | 3',4'-(OMe)₂ | Me | Colorless crystals | >300° C. |  | C₁₉H₁₇NO₅ | | |
|  |  |  |  |  | Calc'd (%) | C 67.25 | H 5.05 | N 4.13 |
|  |  |  |  |  | Found (%) | C 67.34 | H 4.55 | N 4.04 |
| 67 | 3',4'-(OMe)₂ | H | Pale yellow powder | >300° C. |  | C₁₈H₁₅NO₅·H₂O | | |
|  |  |  |  |  | Calc'd (%) | C 62.97 | H 4.99 | N 4.08 |
|  |  |  |  |  | Found (%) | C 62.99 | H 4.71 | N 4.06 |
| 68 | 4'-COOMe | Me | Pale yellow powder | >300° C. |  | C₁₉H₁₅NO₅ | | |
|  |  |  |  |  | Calc'd (%) | C 67.65 | H 4.48 | N 4.15 |
|  |  |  |  |  | Found (%) | C 67.94 | H 4.23 | N 3.86 |
| 69 | 4'-COOH | H | Colorless powder | >300° C. |  | C₁₇H₁₁NO₅ | | |
|  |  |  |  |  | Calc'd (%) | C 66.02 | H 3.59 | N 4.53 |
|  |  |  |  |  | Found (%) | C 65.85 | H 3.60 | N 4.51 |

The compound of example 57 was prepared in the following manner: to 4 grams of 6-cyano-2-(2-methoxyphenyl)-4-quinolone were added 3 grams of potassium hydroxide and 100 ml. of methanol, the mixture was heated to reflux for 4 hours, then poured into ice water. The mixture was adjusted to pH 3 with 10% hydrochloric acid, and crystals which separate out therefrom were collected by filtration and recrystallized from dimethyl formamide to give 2.7 grams of the desired 2-(2-methoxyphenyl)-4-quinolone-6-carboxylic acid, colorless crystals, melting point 290° to 294° C.

The compounds of the table set forth below were produced in an analogous manner to that described herein above.

(Z is a heterocyclic ring)

| Example No. | Z | R³ | Appearance | M.p. | Elementary Analysis |
|---|---|---|---|---|---|
| 70 | 4-Pyridyl | Me | Pale brown crystals | >300° C. | C₁₆H₁₂N₂O₃ |
|  |  |  |  |  | Calc'd (%) C 68.56 H 4.32 N 10.00 |
|  |  |  |  |  | Found (%) C 68.86 H 4.06 N 9.88 |
| 71 | 4-Pyridyl | H | Pale yellow powder | >300° C. | C₁₅H₁₀N₂O₃ |
|  |  |  |  |  | Calc'd (%) C 67.66 H 3.79 N 10.52 |
|  |  |  |  |  | Found (%) C 67.76 H 3.63 N 10.33 |
| 72 | 3-Pyridyl | Me | Colorless crystals | >300° C. | C₁₆H₁₂N₂O₃ |
|  |  |  |  |  | Calc'd (%) C 68.56 H 4.32 N 10.00 |
|  |  |  |  |  | Found (%) C 68.75 H 4.13 N 9.87 |
| 73 | 3-Pyridyl | H | Colorless powder | >300° C. | C₁₅H₁₀N₂O₃ |
|  |  |  |  |  | Calc'd (%) C 67.66 H 3.79 N 10.52 |
|  |  |  |  |  | Found (%) C 67.45 H 3.62 N 10.24 |
| 74 | 2-Pyridyl | Me | Pale brown crystals | >300° C. | C₁₆H₁₂N₂O₃ |
|  |  |  |  |  | Calc'd (%) C 68.56 H 4.32 N 10.00 |
|  |  |  |  |  | Found (%) C 68.85 H 4.20 N 10.02 |
| 75 | 2-Pyridyl | H | Colorless crystals | >300° C. | C₁₅H₁₀N₂O₃ |
|  |  |  |  |  | Calc'd (%) C 67.66 H 3.79 N 10.52 |
|  |  |  |  |  | Found (%) C 67.59 H 3.77 N 10.36 |
| 76 | 2-Furyl | Me | Colorless crystals | >300° C. | C₁₅H₁₁NO₄ |
|  |  |  |  |  | Calc'd (%) C 66.91 H 4.12 N 5.20 |

-continued

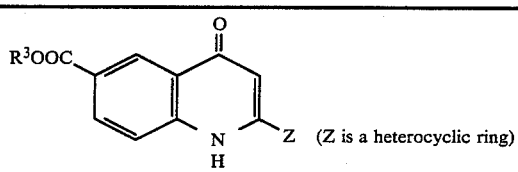

(Z is a heterocyclic ring)

| Example No. | Z | R³ | Appearance | M.p. | Elementary Analysis | | |
|---|---|---|---|---|---|---|---|
| 77 | 2-Furyl | H | Colorless crystals | >300° C. | Found (%) Calc'd (%) | C 67.13 H 3.93 N 5.13 C₁₄H₉NO₄ C 65.88 H 3.55 N 5.49 | |
| 78 | 2-Thienyl | Me | Colorless crystals | >300° C. | Found (%) Calc'd (%) | C 65.75 H 3.42 N 5.40 C₁₅H₁₁NO₃S C 63.16 H 3.89 N 4.91 | |
| 79 | 2-Thienyl | H | Colorless crystals | >300° C. | Found (%) Calc'd (%) Found (%) | C 63.25 H 3.68 N 4.82 C₁₄H₉NO₃S C 61.99 H 3.34 N 5.16 C 61.95 H 3.15 N 5.06 | |

EXAMPLE 80

Ethyl 2-phenyl-4-quinolone-8-carboxylate

A mixture of 7 grams of ethyl benzoylacetate, 6 grams of ethyl anthranilate and 0.5 gram of p-toluenesulfonic acid is dehydrated (by heating) in 300 ml of benzene for three days. Benzene is evaporated therefrom, and the resulting oil is heated at 250° to 280° C. for 0.5 hour in 20 ml of diphenyl ether. After cooling, 250 ml of n-hexane is added thereto, and crystals which separate out therefrom are collected by filtration and recrystallized from methanol to give 4.2 grams of ethyl 2-phenyl-4-quinolone-8-carboxylate, pale brown needles, melting point 218° to 219° C.

Elementary analysis calculated for C₁₇H₁₃NO₃: C 73.11, H 4.69, N 5.02; Found: C 73.04, H 4.85, N 4.81.

Compounds of Examples 81 to 99 are given in the following table.

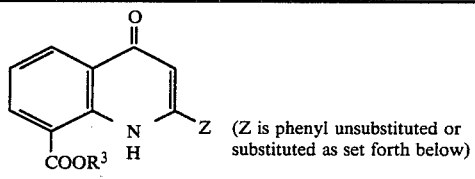

(Z is phenyl unsubstituted or substituted as set forth below)

| Example No. | Substituent(s) on phenyl | R³ | Appearance | M.p | Elementary Analysis |
|---|---|---|---|---|---|
| 81 | H | H | Colorless crystals | 295–296° C. | C₁₆H₁₁NO₃<br>Calc'd (%) C 72.44 H 4.18 N 5.28<br>Found (%) C 72.28 H 3.89 N 5.01 |
| 82 | H | Na | Colorless powder | >300° C. | C₁₆H₁₀NO₃Na.H₂O<br>Calc'd (%) C 62.95 H 3.96 N 4.59<br>Found (%) C 62.68 H 3.99 N 4.33 |
| 83 | 2'-Cl | Et | Colorless needles | 147–148° C. | C₁₈H₁₂ClNO₃<br>Calc'd (%) C 65.96 H 4.31 N 4.27<br>Found (%) C 66.24 H 4.16 N 4.43 |
| 84 | 2'-Cl | Na | Colorless prisms | 262–268° C. | C₁₆H₉ClNO₃Na<br>Calc'd (%) C 59.73 H 2.81 N 4.35<br>Found (%) C 59.55 H 3.00 N 4.23 |
| 85 | 2'-Cl | H | Colorless powder | >300° C. | C₁₆H₁₀ClNO₃<br>Calc'd (%) C 64.12 H 3.36 N 4.67<br>Found (%) C 64.00 H 3.48 N 4.90 |
| 86 | 3'-Cl | Et | Pale yellow needles | 177–178° C. | C₁₈H₁₄ClNO₃<br>Calc'd (%) C 65.96 H 4.31 N 4.27<br>Found (%) C 66.20 H 4.18 N 4.10 |
| 87 | 3'-Cl | H | Colorless powder | >300° C. | C₁₆H₁₀ClNO₃<br>Calc'd (%) C 64.12 H 3.36 N 4.67<br>Found (%) C 64.06 H 3.26 N 4.66 |
| 88 | 2',4'-(Cl)₂ | Me | Colorless crystals | 222–224° C. | C₁₇H₁₁Cl₂NO₃<br>Calc'd (%) C 58.64 H 3.18 N 4.02<br>Found (%) C 58.65 H 3.29 N 3.86 |
| 89 | 2',4'-(Cl)₂ | Et | Pale yellow crystals | 175–177° C. | C₁₈H₁₃Cl₂NO₃<br>Calc'd (%) C 59.68 H 3.62 N 3.88<br>Found (%) C 59.81 H 3.50 N 3.82 |
| 90 | 2',4'-(Cl)₂ | H | Colorless powder | >300° C. | C₁₆H₉Cl₂NO₃<br>Calc'd (%) C 57.51 H 2.71 N 4.19<br>Found (%) C 57.32 H 2.90 N 3.94 |
| 91 | 3',4'-(Cl)₂ | H | Colorless needles | >300° C. | C₁₆H₉Cl₂NO₃<br>Calc'd (%) C 57.51 H 2.71 N 4.19<br>Found (%) C 57.51 H 2.65 N 4.15 |
| 92 | 4'-Me | Et | Pale yellow | 192–193° C. | C₁₈H₁₅NO₃ |

-continued

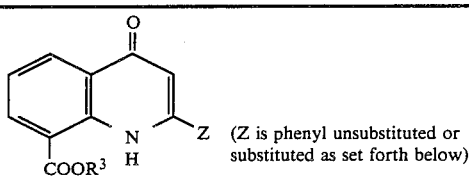
(Z is phenyl unsubstituted or substituted as set forth below)

| Example No. | Substituent(s) on phenyl | R³ | Appearance | M.p | Elementary Analysis |
|---|---|---|---|---|---|
| | | | crystals | | Calc'd (%) C 73.70 H 5.15 N 4.78 |
| | | | | | Found (%) C 73.98 H 5.38 N 4.54 |
| 93 | 4'-Me | H | Colorless crystals | >300° C. | $C_{17}H_{13}NO_3$ |
| | | | | | Calc'd (%) C 73.11 H 4.69 N 5.02 |
| | | | | | Found (%) C 73.16 H 4.52 N 4.92 |
| 94 | 2',4'-(Me)$_2$ | Et | Colorless needles | 125–126° C. | $C_{20}H_{19}NO_3$ |
| | | | | | Calc'd (%) C 74.74 H 5.96 N 4.36 |
| | | | | | Found (%) C 74.71 H 5.79 N 4.33 |
| 95 | 2',4'-(Me)$_2$ | H | Colorless powder | 289–291° C. | $C_{18}H_{15}NO_3$ |
| | | | | | Calc'd (%) C 73.70 H 5.15 N 4.78 |
| | | | | | Found (%) C 73.84 H 5.29 N 4.73 |
| 96 | 4'-n-C$_8$H$_{17}$ | Et | Pale Yellow needles | 94–95° C. | $C_{25}H_{31}NO_3$ |
| | | | | | Calc'd (%) C 77.00 H 7.71 N 3.71 |
| | | | | | Found (%) C 77.07 H 7.69 N 3.62 |
| 97 | 4'-n-C$_8$H$_{17}$ | H | Colorless powder | 202–203° C. | $C_{24}H_{27}NO_3$ |
| | | | | | Calc'd (%) C 76.36 H 7.21 N 3.71 |
| | | | | | Found (%) C 76.57 H 7.21 N 3.82 |
| 98 | 3',4'-(OMe)$_2$ | Et | Colorless needles | 114–116° C. | $C_{20}H_{19}NO_5$ |
| | | | | | Calc'd (%) C 67.98 H 5.42 N 3.96 |
| | | | | | Found (%) C 68.15 H 5.28 N 3.90 |
| 99 | 3',4'-(OMe)$_2$ | H | Colorless needles | 238–240° C. | $C_{19}H_{15}NO_5$ |
| | | | | | Calc'd (%) C 66.45 H 4.65 N 4.31 |
| | | | | | Found (%) C 66.49 H 4.54 N 4.21 |

The compounds set forth hereinbefore can be produced by additional processes. For example, the compound of Example 83, representative of the compounds of the present invention, was prepared as follows:

5 grams of beta-(2-chlorophenyl)-beta-(2-ethoxycarbonylimino)-propionic acid p-ethoxyanilide were added to 80 grams of polyphosphoric acid. The mixture was heated at 140° to 150° C. for 1 hour, cooled, and poured into ice water. The crystals which separate out therefrom were collected by filtration, washed with water, dried and recrystallized from acetone to give 2.3 grams of ethyl 2-(2-chlorophenyl)-4-quinolone-8-carboxylate, pale yellow prisms, melting point 152°–153° C.

EXAMPLE 100

Ethyl 2-(2-chlorophenyl)-4-hydroxyquinoline-8-carboxylate hydrochloride.

Ethyl 2-(2-chlorophenyl)-4-quinolone-8-carboxylate (1.98 gram) is dissolved in 50 ml of methanol, and stirred at room temperature for 0.5 hour with 10 ml of 40% ethanolic hydrochloric acid. The solvent is evaporated from the solution, and the residue is recrystallized from ethanol to give 1.9 grams of ethyl 2-(2-chlorophenyl)-4-hydroxyquinoline-8-carboxylate hydrochloride, colorless prisms, melting point 196° to 198° C.

Elementary analysis calculated for $C_{18}H_{15}NO_3Cl_2$: C 59.36, H 4.15, N 3.85; Found: C 59.34, H 4.08, H 3.87.

EXAMPLE 101

Methyl 2-(2-chlorophenyl)-4-quinolone-8-carboxylate

A solution of 10 grams of alpha-(2-chlorobenzoyl)-3-methoxycarbonyl-2-nitroacetophenone in 50 ml of glacial acetic acid was dropped into a solution of 25 grams of stanneous chloride in 50 ml of concentrated hydrochloric acid with stirring. The mixture was then slightly warmed to make it transparent and allowed to stand overnight. The crystals which separate out therefrom were collected by filtration, dissolved in warm diluted alkaline solution, and filtered. To the filtrate was added ammonium chloride and ammonia water, the mixture was vigorously stirred, and the crystals which separate out were collected by filtration. The crystals were washed with water, dried and recrystallized from acetone to give 1.2 grams of the title product, yellow needles, melting point 166° to 168° C.

Alternatively, to 8 grams of dimethyl 2-aminoisophthalate was added 9.2 grams of o-chloroacetophenone diethylacetal, the mixture was heated at 140° C. for 30 minutes, then at 200° C. for additional 20 minutes, and finally heated to reflux for 18 hours. The reaction mixture was cooled, crystals separated out were collected by filtration, and recrystallized from acetone to give 2.8 grams of the title product, melting point 166°–168° C.

As a further alternative, 2.8 grams of o-chlorobenzaldehyde and 50 ml of glacial acetic acid were added to 5.1 grams of 2-amino-3-methoxycarbonyl-alpha-(methylsulfinyl)-acetophenone. The mixture was heated at 75° to 80° C. for one hour, cooled, poured into water, and the crystals which separate out therefrom were collected by filtration, washed with water and recrystallized from acetone to give 1 gram of the title product, melting point 166°–168° C.

The compounds of Examples 102 to 108 are produced by the processes above described.

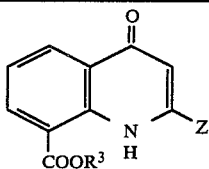

| Example Number | Substituent on Phenyl group | R³ | Appearance | Melting Point |
|---|---|---|---|---|
| 102 | 2'-Cl | Et | Pale Yellow Needles | 164–166° C. |
| 103 | 4'-Cl | Et | Colorless Needles | 190–230° C. |
| 104 | 2'-Me | Et | Colorless Crystals | 119–123° C. |
| 105 | 3',4'-(Me)₂ | Et | Pale Yellow Needles | 210–211° C. |
| 106 | 4'-iso-Pr | Et | Yellow Needles | 148–149° C. |
| 107 | 4'-Me | Et | Yellow Needles | 192–194° C. |
| 108 | 2',4'-(OMe)₂ | Et | Pale Yellow Needles | 160–162° C. |

EXAMPLE 109

Beta-Hydroxyethyl 2-(2-chlorophenyl)-4-quinolone-8-carboxylate.

2-(2-Chlorophenyl)-4-quinolone-8-carboxylic acid (10 grams) was stirred overnight at 95° to 98° C. in a mixture of 10 ml of concentrated sulfuric acid and 100 ml of ethylene glycol. The reaction solution was poured over into water and separated crystals were collected by filtration and then washed with water. After dried, the crystals were re-crystallized from acetone to give 8.2 grams of the title compounds, pale yellow prisms, melting point 170° to 171° C.

EXAMPLE 110

Allyl 2-(2-chlorophenyl)-4-quinolone-8-carboxylate.

To 7 grams of the potassium salt of 2-(2-chlorophenyl)-4-quinolone-8-carboxylic acid were added 2 ml of allyl bromide and 200 ml of dimethyl formamide, the mixture was stirred at 70° to 80° C. for 6 hours, and poured into water. The mixture was extracted with chloroform, the solvent was removed from the extract, and the residue was recrystallized from acetone to give 5.6 grams of the title compound, pale yellow needles, melting point 121° C.

The compounds of Examples 109 and 100 are produced by the processes above described.

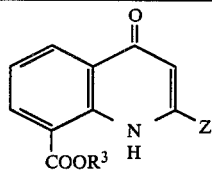

| Example Number | Substituent on a phenyl group | R³ | Appearance | Melting Point |
|---|---|---|---|---|
| 111 | 2'-Cl | n-C₃H₇ | Pale yellow prisms | 138° C. |
| 112 | 2'-Cl | iso-C₄H₉ | Colorless Prisms | 107° C. |
| 113 | 2'-Cl | n-C₆H₁₃ | Pale yellow columns | 72° C. |
| (114 not given) | | | | |
| 115 | 2'-Cl | (CH₂)₃OH | Colorless Needles | 169–170° C. |
| 116 | 2'-Cl | (CH₂)₅OH | Colorless crystals | 99–105° C. |
| 117 | 2'-Cl | (CH₂)₆OH | Colorless crystals | 98–103° C. |
| 118 | 2'-Cl | (CH₂)₂OAc | Colorless powder | 122–124° C. |
| 119 | 2'-Cl | (CH₂)₂OPh | Pale yellow prisms | 163° C. |
| 120 | 2'-Cl | (CH₂)₂OEt | Pale brown crystals | 90–91° C. |
| 121 | 2'-Cl | CH₂CN | Yellow needles | 225–227° C. |
| 122 | 2'-Cl | CH₂COCH₃ | Colorless crystals | 155° C. |
| 123 | 2'-Cl | CH₂COOEt | Pale yellow needles | 93.5–94.5° C. |
| 124 | 2'-Cl | (CH₂)₃COOEt | Colorless prisms | 102° C. |
| 125 | 2'-Cl | CH₂CH(OH)CH₃ | Pale yellow crystals | 174–177° C. |
| 126 | 2'-Cl | CH₂CH(OH)CH₂OH | Pale brown crystals | 171–173° C. |
| 127 | 2'-Cl | (CH₂)₂O—iso-Bu | Colorless crystals | 90–93° C. |
| 128 | 2'-Cl | (CH₂)₂O(CH₂)₂OH | Colorless prisms | 133–134° C. |
| 129 | 2'-Cl | (CH₂)₂O(CH₂)₂OEt | Colorless crystals | 65–67° C. |
| 130 | 2'-Cl | CH₂COCH₂COOEt | Pale brown crystals | 122–123° C. |
| 131 | 2'-F | CH₂CH₂OH | Pale yellow crystals | 159–161° C. |
| 132 | 3'-Cl | CH₂CH₂OH | Colorless crystals | 186–190° C. |
| 133 | 4'-Cl | CH₂CH₂OH | Colorless crystals | 216–218° C. |
| 134 | 2'-Me | CH₂CH₂OH | Colorless crystals | 160–163° C. |
| 135 | 4'-Me | CH₂CH₂OH | Colorless crystals | 213–216° C. |
| 136 | 2', 4'-Me₂ | CH₂CH₂OH | Pale yellow plates | 175–176° C. |
| 137 | 3', 4'-Me₂ | CH₂CH₂OH | Pale yellow needles | 185–187° C. |
| 138 | 4'-OMe | CH₂CH₂OH | Colorless needles | 196–198° C. |
| 139 | 2', 4'-(OMe)₂ | CH₂CH₂OH | Pale yellow needles | 175–177° C. |
| 140 | 3', 4'-(OMe)₂ | CH₂CH₂OH | Pale yellow needles | 212–213° C. |

What we claim is:

1. A compound of the formula (I):

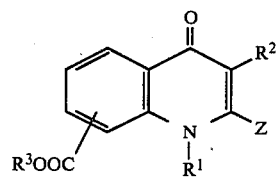

or a pharmaceutically aceptable salt thereof, wherein R¹ and R² are each hydrogen, alkyl of 1 to 8 carbon atoms or alkenyl of 2 to 4 carbon atoms; R³ is hydrogen, alkyl of 1 to 8 carbon atoms unsubstituted or substituted by one or two hydroxyl moieties, alkyl of 3 to 10 carbon atoms with one or two ether bonds unsubstituted or substituted by 1 hydroxyl group or —$(CH_2)_nA$ wherein n is an integer of 1 to 3 and A is acetyl, acetoxy, ethoxycarbonyl, ethoxycarbonylacetyl, cyano or phenoxy, phenylethyl or allyl; and Z is phenyl unsubstituted or substituted by one or two halo atoms, one or two alkyl moieties of 1 to 8 carbon atoms, haloalkyl of 1 to 3 carbon atoms, one or two alkoxy moieties of 1 to 4 carbon atoms or $COOR^4$ wherein $R^4$ is hydrogen or alkyl of 1 to 4 carbon atoms; or Z is pyrrolyl, pyrrolinyl, pyridyl, furyl or thienyl.

2. A compound according to claim 1 wherein Z is phenyl, 2-fluorophenyl, 2-chlorophenyl, 3-chlorophenyl, 4-chlorophenyl, 2-bromophenyl, 2-iodophenyl, 2,4-dichlorophenyl, 3,4-dichlorophenyl, 2,5-dichlorophenyl, o-tolyl, p-tolyl, 2-ethylphenyl, 4-isopropylphenyl, 4-pentylphenyl, 2,4-dimethylphenyl, 3-trifluoromethylphenyl, 2-methoxyphenyl, 4-methoxyphenyl, 2-ethoxyphenyl, 2-isopropoxyphenyl, 2,4-dimethoxyphenyl, 3,4-dimethoxyphenyl, 4-carboxyphenyl, 4-methoxycarbonylphenyl, pyrrolyl, pyrrolinyl, pyridyl, furyl or thienyl.

3. A pharmaceutical composition useful for effecting anti-inflammatory, anti-allergenic, antitussive, expectorant and antithrombotic action in humans and animals which comprises a therapeutically effective amount of a compound of the formula (I):

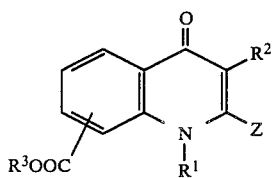

or a pharmaceutically acceptable salt thereof, wherein $R^1$ and $R^2$ are each hydrogen, alkyl of 1 to 8 carbon atoms or alkenyl of 2 to 4 carbon atoms; $R^3$ is hydrogen, alkyl of 1 to 8 carbon atoms unsubstituted or substituted by one or two hydroxyl moieties, alkyl of 3 to 10 carbon atoms with one or two ether bonds unsubstituted or substituted by 1 hydroxyl group or —$(CH_2)_nA$ wherein n is an integer of 1 to 3 and A is acetyl, acetoxy, ethoxycarbonyl, ethoxycarbonylacetyl, cyano or phenoxy, phenylethyl or allyl; and Z is phenyl unsubstituted or substituted by one or two halo atoms, one or two alkyl moieties of 1 to 8 carbon atoms, haloalkyl of 1 to 3 carbon atoms, one or two alkoxy moieties of 1 to 4 carbon atoms or $COOR^4$ wherein $R^4$ is hydrogen or alkyl of 1 to 4 carbon atoms; or Z is pyrrolyl, pyrrolinyl, pyridyl, furyl or thienyl, in combination with a pharmaceutically acceptable carrier.

4. A composition according to claim 3 wherein Z is phenyl, 2-fluorophenyl, 2-chlorophenyl, 3-chlorophenyl, 4-chlorophenyl, 2bromophenyl, 2-iodophenyl, 2,4-dichlorophenyl, 3,4-dichlorophenyl, 2,5-dichlorophenyl, o-tolyl, p-tolyl, 2-ethylphenyl, 4-isopropylphenyl, 4-pentylphenyl, 2,4-dimethylphenyl, 3-trifluoromethylphenyl, 2-methoxyphenyl, 4-methoxyphenyl, 2-ethoxyphenyl, 2-isopropoxyphenyl, 2,4-dimethoxyphenyl, 3,4-dimethoxyphenyl, 4-carboxyphenyl, 4-methoxycarbonylphenyl, pyrrolyl, pyrrolinyl, pyridyl, furyl or thienyl.

5. A method of effecting anti-inflammatory, anti-allergenic, antitussive, expectorant and antithromotic action in humans and animals which comprises administering to a human or animal in need thereof a therapeutically effective amount of a compound of the formula (I):

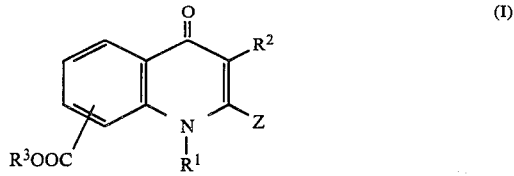

or a pharmaceutically acceptable salt thereof, wherein $R^1$ and $R^2$ are each hydrogen, alkyl of 1 to 8 carbon atoms or alkenyl of 2 to 4 carbon atoms; $R^3$ is hydrogen, alkyl of 1 to 8 carbon atoms unsubstituted or substituted by one or two hydroxyl moieties, alkyl of 3 to 10 carbon atoms with one or two ether bonds unsubstituted or substituted by 1 hydroxyl group or —$(CH_2)_nA$ wherein n is an integer of 1 to 3 and A is acetyl, acetoxy, ethoxycarbonyl, ethoxycarbonylacetyl, cyano or phenoxy, phenylethyl or allyl; and Z is phenyl unsubstituted or substituted by one or two halo atoms, one or two alkyl moieties of 1 to 8 carbon atoms, haloalkyl of 1 to 3 carbon atoms, one or two alkoxy moieties of 1 to 4 carbon atoms or $COOR^4$ wherein $R^4$ is hydrogen or alkyl of 1 to 4 carbon atoms; or Z is pyrrolyl, pyrrolinyl, pyridyl, furyl or thienyl, in combination with a pharmaceutically acceptable carrier.

6. A method according to claim 5 wherein Z is phenyl, 2-fluorophenyl, 2-chlorophenyl, 3-chlorophenyl, 4-chlorophenyl, 2-bromophenyl, 2-iodophenyl, 2,4-dichlorophenyl, 3,4-dichlorophenyl, 2,5-dichlorophenyl, o-tolyl, p-tolyl, 2-ethylphenyl, 4-isopropylphenyl, 4-pentylphenyl, 2,4-dimethylphenyl, 3-trifluoromethylphenyl, 2-methoxyphenyl, 4-methoxyphenyl, 2-ethoxyphenyl, 2-isopropoxyphenyl, 2,4-dimethoxyphenyl, 3,4-dimethoxyphenyl, 4-carboxyphenyl, 4-methoxycarbonylphenyl, pyrrolyl, pyrrolinyl, pyridyl, furyl or thienyl.

7. The compound according to claim 1 of the formula

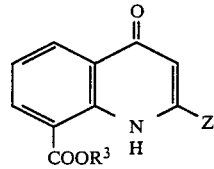

wherein Z is 2-chlorophenyl and $R^3$ is ethyl.

8. The compound according to claim 1 of the formula

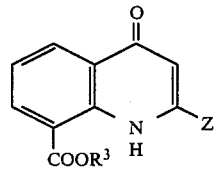

wherein Z is 3,4-dimethylphenyl and $R^3$ is ethyl.

9. The compound according to claim 1 which is Beta-hydroxyethyl 2-(2-chlorophenyl)-4-quinolone-8-carboxylate.

10. The compound according to claim 1 of the formula

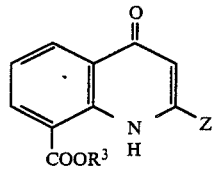

wherein Z is 2-chlorophenyl and R³ is (CH₂)₂OAc.

11. The compound according to claim 1 of the formula

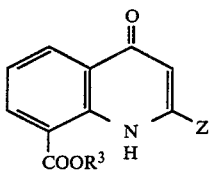

wherein Z is 2-chlorophenyl and R³ is (CH₂)₂OEt.

12. The compound according to claim 1 of the formula

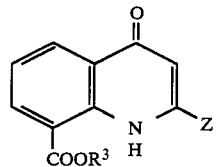

wherein Z is 2-chlorophenyl and R³ is CH₂COCH₃.

13. The compound according to claim 1 of the formula

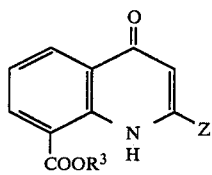

wherein Z is 2-chlorophenyl and R³ is CH₂CH(OH)CH₂OH.

14. A compound of the formula wherein Z is 2-chlorophenyl and R³ is CH₂CH(OH)CH₃.

15. A compound according to claim 2 wherein R² is hydrogen.

16. A composition according to claim 4 wherein R² is hydrogen.

17. A method according to claim 6 wherein R² is hydrogen.

* * * * *